United States Patent
McEntire et al.

(10) Patent No.: US 12,070,391 B2
(45) Date of Patent: Aug. 27, 2024

(54) METHOD FOR IMPROVING THE WEAR PERFORMANCE OF CERAMIC-POLYETHYLENE OR CERAMIC-CERAMIC ARTICULATION COUPLES UTILIZED IN ORTHOPEDIC JOINT PROSTHESES

(71) Applicant: SINTX Technologies, Inc., Salt Lake City, UT (US)

(72) Inventors: Bryan J. McEntire, Salt Lake City, UT (US); Ryan M. Bock, Salt Lake City, UT (US)

(73) Assignee: SINTX Technologies, Inc., Salt Lake City, UT (US)

( * ) Notice: Subject to any disclaimer, the term of this patent is extended or adjusted under 35 U.S.C. 154(b) by 0 days.

(21) Appl. No.: 17/839,092

(22) Filed: Jun. 13, 2022

(65) Prior Publication Data
US 2022/0304811 A1    Sep. 29, 2022

Related U.S. Application Data

(63) Continuation of application No. 16/380,426, filed on Apr. 10, 2019, now abandoned.
(Continued)

(51) Int. Cl.
| | |
|---|---|
| A61F 2/30 | (2006.01) |
| A61F 2/34 | (2006.01) |
| A61L 27/10 | (2006.01) |
| A61F 2/36 | (2006.01) |
| A61L 31/02 | (2006.01) |

(52) U.S. Cl.
CPC ........ A61F 2/30767 (2013.01); A61F 2/3094 (2013.01); A61F 2/34 (2013.01); A61L 27/10 (2013.01); A61F 2/36 (2013.01); *A61F 2310/00317* (2013.01); *A61L 31/026* (2013.01); *A61L 2400/10* (2013.01); *A61L 2420/02* (2013.01); *A61L 2430/24* (2013.01)

(58) Field of Classification Search
CPC ............ H01L 29/517; H01L 21/76218; A61L 27/446; A61F 2/30767
See application file for complete search history.

(56) References Cited

U.S. PATENT DOCUMENTS

| | | | |
|---|---|---|---|
| 5,234,642 A | 8/1993 | Nishioka et al. | |
| 2007/0207628 A1* | 9/2007 | Chua ................ | H01L 21/02337 257/E21.268 |

(Continued)

FOREIGN PATENT DOCUMENTS

JP    2003226581 A    8/2003

OTHER PUBLICATIONS

Pezzoti et al., On the molecular interaction between femoral heads and polyethylene liners in artificial hip joints: phenomenology and molecular scale phenomena, Biomedical Materials, vol. 12, 2017, pp. 1-13 (Year: 2017).*

(Continued)

*Primary Examiner* — Robert S Walters, Jr.
*Assistant Examiner* — Andrew J Bowman
(74) *Attorney, Agent, or Firm* — Polsinelli PC

(57) ABSTRACT

Methods for improving the wear performance of silicon nitride and/or other ceramic materials, particularly to make them more suitable for use in manufacturing biomedical implants.

15 Claims, 25 Drawing Sheets
(23 of 25 Drawing Sheet(s) Filed in Color)

Related U.S. Application Data

(60) Provisional application No. 62/655,457, filed on Apr. 10, 2018.

(56) References Cited

U.S. PATENT DOCUMENTS

2010/0049331 A1 2/2010 Khandkar
2016/0339144 A1* 11/2016 McEntire .............. A61L 27/446

OTHER PUBLICATIONS

Proverbio et al., Low-Temperature Oxidation of Silicon Nitride by Water in Supercritical Condition, Journal of European Ceramic Society, 1996, vol. 16, pp. 1121-1126 (Year: 1996).*
Lee et al., Hydrothermal Treatment of Si3N4 for the Improvement of Oxidation Resistance at 1400C, Journal of Ceramic Society, 2008, vol. 91, No. 2, pp. 679-682 (Year: 2008).*
E1, Autoclave Temperature and Time Pressure Chart, 2022, Sterilizers. clm, pp. 1-3 (Year: 2022).*
Pezzoti et al., On the molecular interaction between femoral heads and polyethylene liners in artificial hip joints:phenomenology and molecular scale phenomena, Biomedical Materials, 2017, No. 12, pp. 1-13 (Year: 2017).*
Japan Patent Office, Notice of Reason for Rejection, Application No. JP 2020-555312, date Mar. 7, 2023, 6 pages.
Patent Cooperation Treaty, International Search Report and Written Opinion issued in corresponding Application No. PCT/US2019/026789 dated Jun. 27, 2019, 9 pages.
European Patent Office, Extended European Search Report issued in related Application No. 19785574.5 on Nov. 29, 2021, 11 pages.
National Institute of Industrial Property (INPI), Preliminary Office Action, Application No. BR112020019575-8, Mar. 21, 2023, 5 pages.
Sudhir, B. et al., Effect of Steam Velocity on the Hydrothermal Oxidation/Volatilization of Silicon Nitride, Journal of the American Ceramic Society, vol. 89, No. 4, Apr. 2006, pp. 1380-1387.
IP Australia, Examination Report No. 1, Application No. 2019252130, dated Nov. 21, 2023, 4 pages.
Japan Patent Office, Notice of Reasons for Rejection, Application No. 2020-555312, dated Oct. 3, 2023, 4 pages.
Canadian Intellectual Property Office, Official Acton, Application No. 3,094,146, dated Oct. 20, 2023, 5 pages.
Pezzotti G. et al., "On the molecular interaction between femoral heads and polyethylene liners in artificial hip joints: phenomenology and molecular scale phenomena," Biomedical Materials, vol. 12, Dec. 2, 2016, 13 pages.
Korean Intellectual Property Office, Notification of Provisional Rejection, Application No. 10-2020-7028546, Jan. 5, 2024, 12 pages.

* cited by examiner

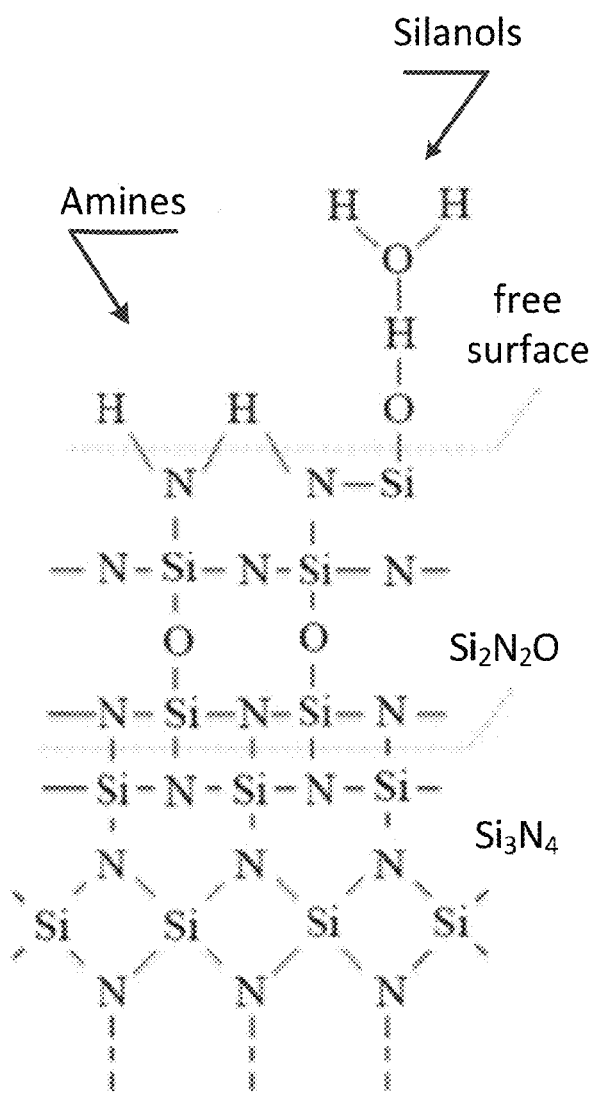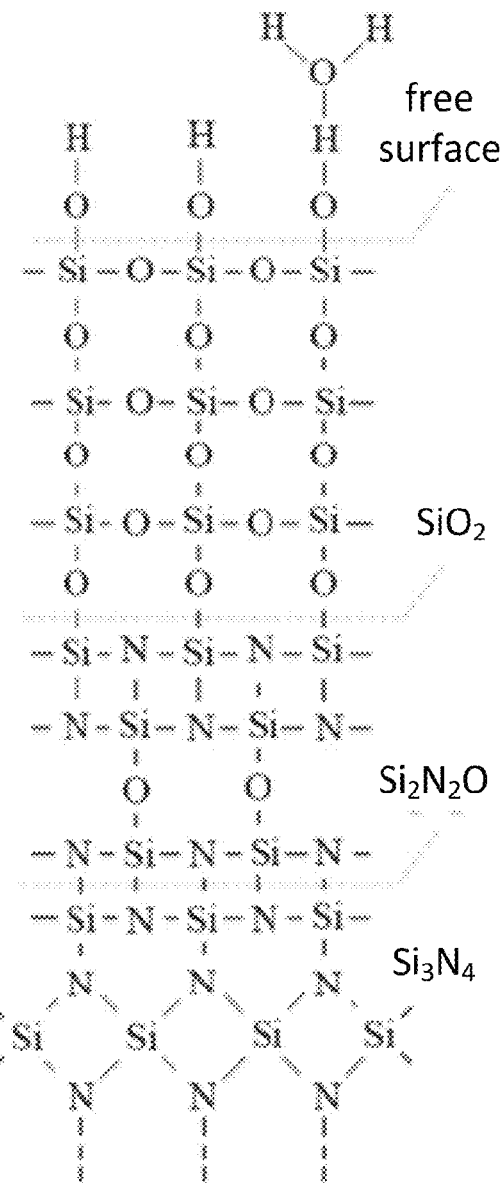
FIG. 1A
FIG. 1B

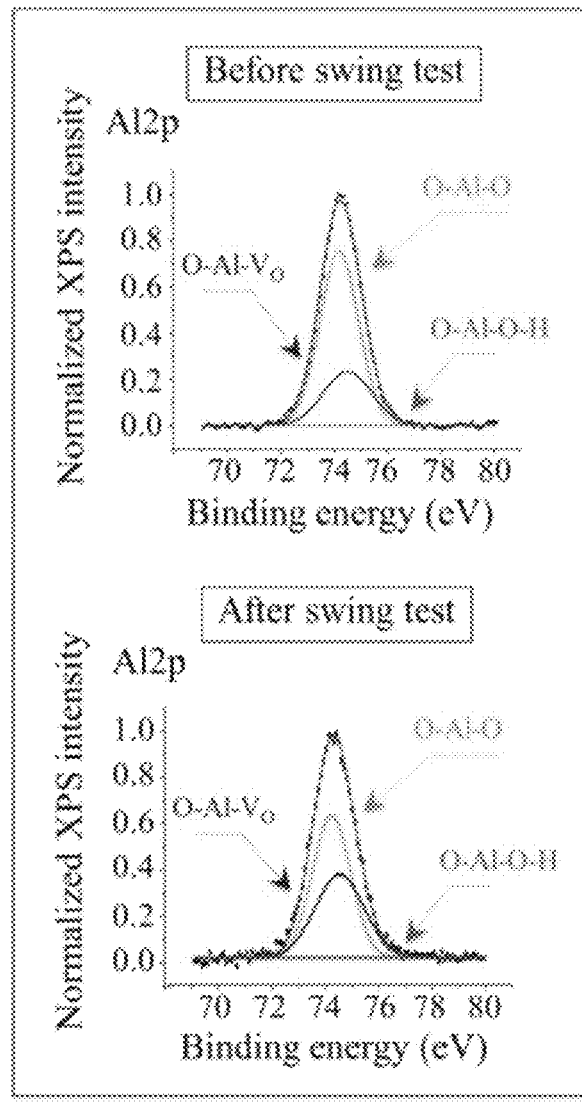
FIG. 13A
FIG. 13B
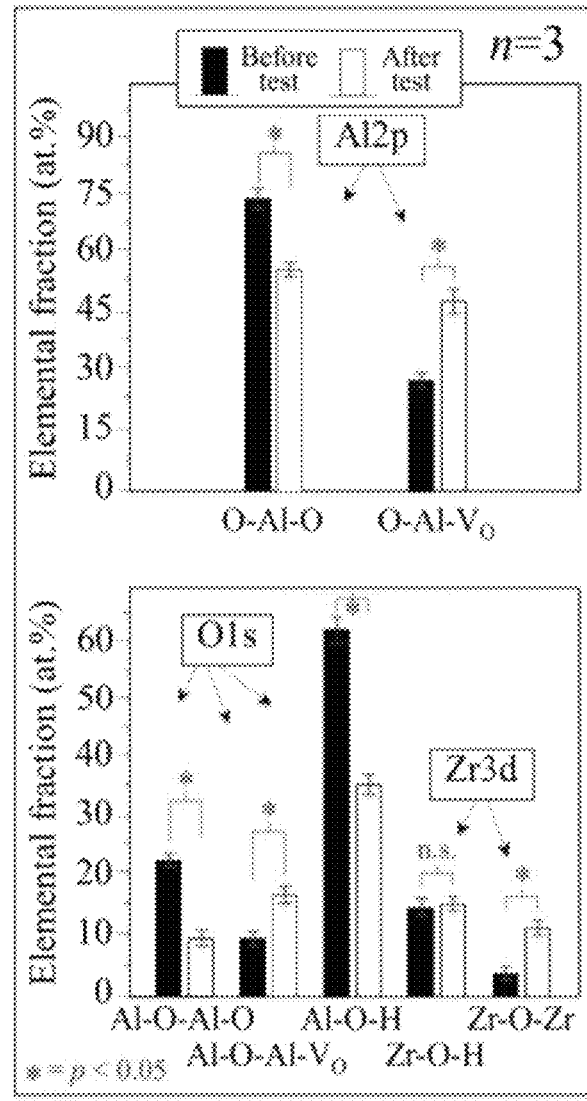
FIG. 13C
FIG. 13D

FIG. 14A
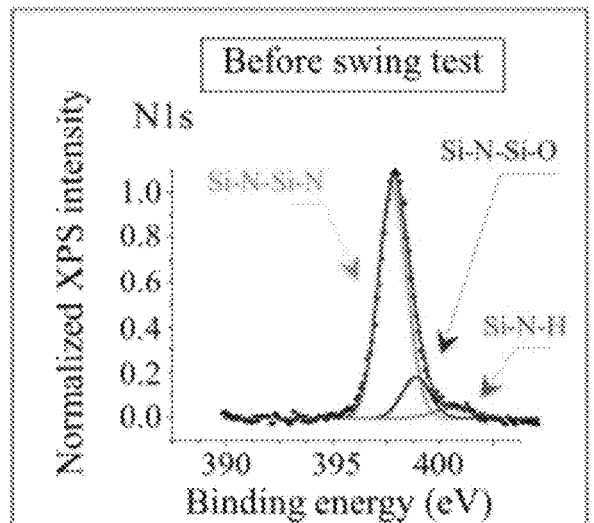
FIG. 14B
FIG. 14C
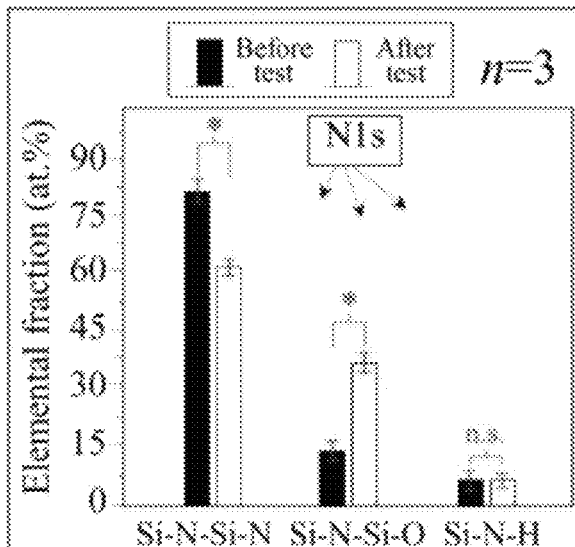
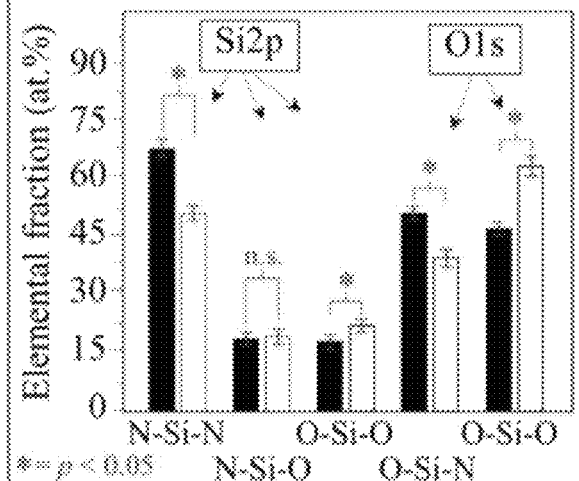
FIG. 14D

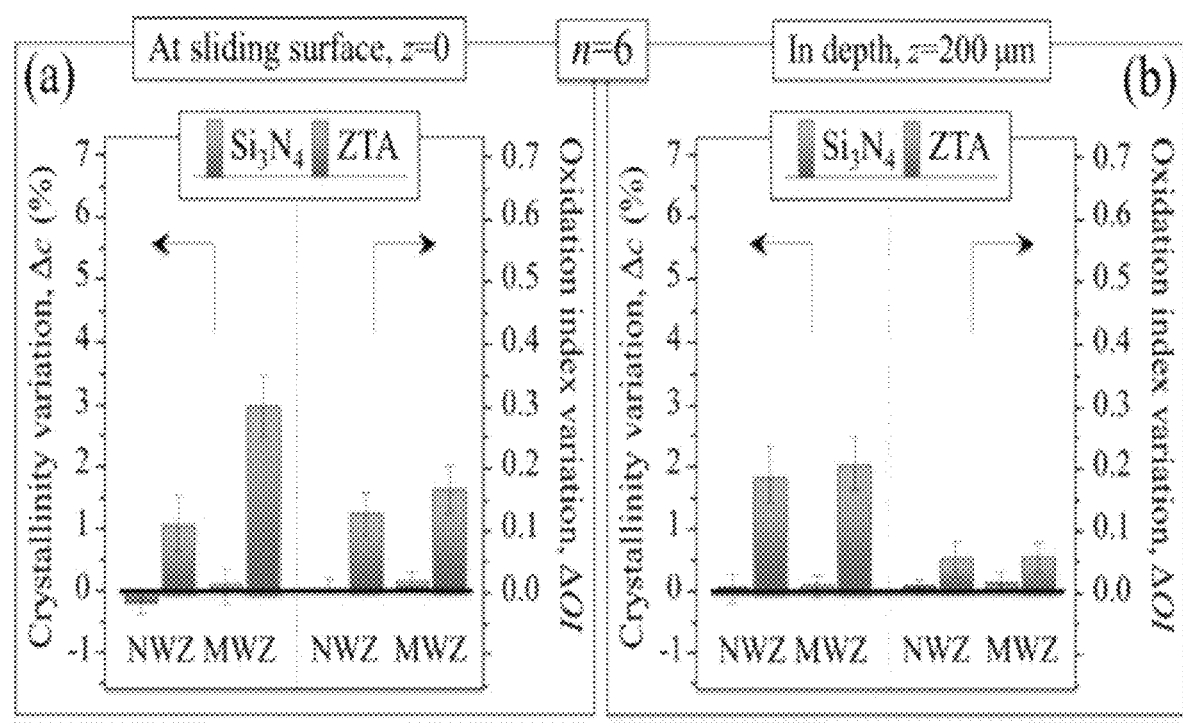
FIG. 17A  FIG. 17B

METHOD FOR IMPROVING THE WEAR PERFORMANCE OF CERAMIC-POLYETHYLENE OR CERAMIC-CERAMIC ARTICULATION COUPLES UTILIZED IN ORTHOPEDIC JOINT PROSTHESES

CROSS REFERENCE TO RELATED APPLICATION

This application is a continuation patent application of U.S. patent application Ser. No. 16/380,426; filed Apr. 10, 2019 that claims priority to U.S. Provisional Application No. 62/655,457, filed Apr. 10, 2018, the contents of which are entirely incorporated by reference herein.

FIELD

The present disclosure generally relates to methods for producing silicon oxynitride materials that have improved polyethylene wear performance.

BACKGROUND

Orthopedic reconstructive surgeries, including total hip (THA), total knee (TKA), or total shoulder (TSA) arthroplasty, are proven procedures for treatment of various end-stage degenerative osteoarthropathy conditions. These therapies involve the replacement of native biological articulation tissues with abiotic biomaterials. Typical THA prosthetic devices include mobile metallic or ceramic heads articulating against stationary polyethylene counterfaces (MoP or CoP, respectively). Other variations include ceramic-on-ceramic (CoC) devices. While the longevity of these prostheses are reasonable (i.e., 10-15 years), their failure is generally associated with excessive polyethylene wear, ceramic wear, or component damage which results in aseptic loosening, osteolysis, and/or osteomyelitis. Revision surgery (an unwanted and expensive secondary procedure for both the surgeon and hospital) is then required to replace the worn components, often resulting in poorer ambulatory function with added comorbidities for the patient. Therefore, there is a need for materials that have increased wear performance that can be used in prostheses.

It is with these observations in mind, among others, that various aspects of the present disclosure were conceived and developed.

SUMMARY OF THE INVENTION

One aspect of the present disclosure encompasses a silicon oxynitride material, wherein the silicon oxynitride material has improved wear performance. The silicon oxynitride material is prepared by a process comprising forming a silicon nitride material block and oxidizing the silicon nitride material block.

Other aspects and features of the invention will be in part apparent and in part pointed out hereinafter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A and FIG. 1B depict schematic diagrams for the surface chemistry of $Si_3N_4$ ceramics: (FIG. 1A) prior to hydrothermal oxidation; and, (FIG. 1B) after hydrothermal oxidation. Note the reduced concentration of amines and increased concentration of silanols and silica ($SiO_2$) bonding in the hydrothermally oxidized surface.

FIG. 2E, FIG. 2F, FIG. 2G, and FIG. 2H show deconvolution of the O1s band. FIG. 2E, FIG. 2F, FIG. 2G, and FIG. 2H show deconvolution of the $Si_2P$ band.

(FIG. 6A) at the sliding surface, z=0 μm; and (FIG. 6B) at a depth of z=200 μm.

FIG. 13A shows XPS (Al2p) analyses of ZTA femoral heads before frictional swing testing against X3 UHMWPE liners for $5 \times 10^5$ cycles at 1 Hz. FIG. 13B shows XPS (Al2p) analyses of ZTA femoral heads after frictional swing testing against X3 UHMWPE liners for $5 \times 10^5$ cycles at 1 Hz. FIG. 13C shows quantitative bond fractions are given in (Al2p). FIG. 13D shows quantitative bond fractions are given in (O1s and Zr3d).

FIG. 14A shows XPS (N1s) analyses of $Si_3N_4$ femoral heads before frictional swing testing against X3 UHMWPE liners for $5 \times 10^5$ cycles at 1 Hz. FIG. 14B shows XPS (N1s) analyses of $Si_3N_4$ femoral heads after frictional swing testing against X3 UHMWPE liners for $5 \times 10^5$ cycles at 1 Hz. FIG. 14C shows quantitative bond fractions are given in (N1s). FIG. 14D shows quantitative bond fractions are given in (Si2p and O1s).

FIG. 17A shows crystallinity and oxidation variations observed at the surfaces of vitamin E-doped UHMWPE liners coupled to $Si_3N_4$ and ZTA femoral heads after being subjected to a $5 \times 10^6$ cycles in a standard hip simulator test. FIG. 17B shows crystallinity and oxidation variations observed at 200 μm in the depth of vitamin E-doped UHMWPE liners coupled to $Si_3N_4$ and ZTA femoral heads after being subjected to a $5 \times 10^6$ cycles in a standard hip simulator test.

Corresponding reference characters indicate corresponding elements among the view of the drawings. The headings used in the figures do not limit the scope of the claims.

DETAILED DESCRIPTION

Figure 2A:
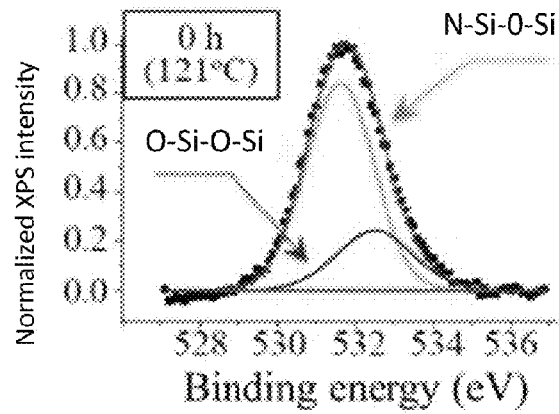
FIG. 2A, FIG. 2B, FIG. 2C, FIG. 2D, FIG. 2E, FIG. 2F, FIG. 2G, and FIG. 2H depict graphs showing x-ray photoelectron spectroscopy (XPS) results for hydrothermally-treated silicon nitride surfaces after 0 (FIG. 2A and FIG. 2E), 24 (FIG. 2B and FIG. 2F), 48 (FIG. 2C and FIG. 2G), and 72 (FIG. 2D and FIG. 2H) hours of exposure to the hydrothermal oxidation process.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

Several definitions that apply throughout the above disclosure will now be presented. As used herein, "improved wear performance" means an improvement in the longevity of the material or device over existing THA prosthetic devices. For example, "improved wear performance" means the material and/or device has a longevity of greater than 10-15 years after being implanted in a patient. The terms "comprising," "including" and "having" are used interchangeably in this disclosure. The terms "comprising," "including" and "having" mean to include, but not necessarily be limited to the things so described.

There are crucial physical chemistry characteristics of biomaterial surfaces that directly affect their long-term performance as artificial joints. Non-oxide bioceramics, such as silicon nitride, may possess favorable surface chemistry that naturally protects a polyethylene-sliding counter-surface from oxidation. A key concept in establishing this favorable chemistry is the control of the oxygen activity at the bioceramic surface during tribochemical loading in the otherwise anaerobic body environment.

Ceramic oxides, which are comprised of metal and oxygen elements, exhibit significant affinity for water because of highly synergic hydrogen bonding at the liquid/solid interface. In the case of alumina ($Al_2O_3$), a peculiar near-surface electronic state provides multiple H-bonding, which results in complete wetting—a positive phenomenon in hip-joint tribology. However, this same pecu-liarity leads to complex patterns of surface hydroxylation and dehydroxylation in thermally- or frictionally-activated environments. Hydroxylation and dehydroxylation are key events in rationalizing surface charge issues; they play important roles in frictional interactions, although their precise microscopic mechanisms are presently unknown. The incorporation of water into the $Al_2O_3$ crystal structure results in the formation of aluminum hydroxide. Dissolution of alumina via amphoteric ionization reactions frees oxygen and forms oxygen vacancies within the alumina lattice. The subsequent release of soluble Al species as hydrolysis products is dependent on both pH and temperature. Conversely, hydrothermal interactions between non-oxide ceramics and their environment is mainly driven by oxidation of their cation elements. In the case of silicon nitride ($Si_3N_4$), surface reactions start with homolytic cleavage of the covalent bond between silicon and nitrogen, followed by oxidation of the silicon sites, and the release of nitrogen as ammonia. During frictional loading in an aqueous environment, a layer of insoluble tribo-products (i.e., hydrated silicon oxides) forms at the solid surface. Collectively, they act as a lubricant in frictional sliding by forming a protective film. The advantage of this hydrated layer in reducing friction is similar to that of the hydrated layer in $Al_2O_3$. However, this is where the similarity ends. Oxygen is attracted to the non-oxide ceramic's surface (at Si sites) rather than being released (as is the case for $Al_2O_3$), while nitrogen reacts with hydrogen to form volatile ammonia. Moreover, the amphoteric silica layer formed at the surface of $Si_3N_4$ acts as an Arrhenius acid with water being the corresponding Arrhenius base. Also, the surface charge of $Si_3N_4$ depends on the pH of the environment; its isoelectric point resides at extremely acidic values (pH=1.2-4). Conversely, $Al_2O_3$ has a point of zero charge at relatively high alkaline values (pH=8-8.5). The silica layer that develops at the $H_2O$-chemisorbed surface of $Si_3N_4$ can easily dissolve because it is considerably more acidic than water, (i.e., its solubility is ~100 times that of $Al_2O_3$), but oxygen is tightly bound as orthosilicic acid chains. In essence, water adsorption at the surface of ceramics acts as a solvent for oxides and as an oxidant for non-oxides. In both cases, the final products of these aqueous surface reactions are hydrated species (i.e., aluminum hydroxides and orthosilicic acid for $Al_2O_3$ and $Si_3N_4$, respectively). Both act as lubricants to reduce friction during tribological sliding. While this common characteristic makes both oxide and non-oxide ceramics suitable as low-friction artificial joint materials, they substantially differ in the direction of oxygen flow across the tribolayer. Specifically, oxygen moves away from the $Al_2O_3$ surface and moves towards the $Si_3N_4$ surface. This difference is crucial when the sliding counterpart in the artificial joint is polyethylene.

The oxygen released from various oxide ceramics' surfaces may lead to the oxidation of advanced polyethylene liners. Silicon nitride with oxidized surfaces (silicon oxynitride) may have a much lower impact on polyethylene liner oxidation and may provide an "ionic protective" effect. Silicon nitride ceramics in femoral heads may delay oxidation of polyethylene liners. Therefore the ultimate lifetime of artificial joints may be improved by the use of silicon nitride femoral heads with an oxidized surface.

(I) Silicon Oxynitride Materials

An aspect of the present disclosure encompasses silicon oxynitride materials that have improved wear performance or characteristics. In general, the silicon oxynitride materials may be formed by oxidizing the surface of a silicon nitride material.

The silicon oxynitride material may form a biomedical implant or part of a biomedical implant in various embodiments. In preferred embodiments, silicon oxynitride material implants, may therefore be provided that may, in some embodiments, be treated so as to improve upon their wear characteristics, water wettability, and/or other desirable characteristics.

In other embodiments, the silicon oxynitride material may comprise an unfinished piece of material that will ultimately be shaped, machined, or otherwise formed into a suitable shape and/or configuration to serve as one of the above-referenced finished biomedical implants. In some such embodiments, the unfinished piece may require one or more additional processing steps before it can be considered completed and ready for implantation. For example, in some embodiments, the biomedical implant may comprise only a part or portion of what will eventually become a finished biomedical implant. In one embodiment, the biomedical implant is an articulation component. Examples of articulation components may be, without limit, femoral heads, femoral condyles, acetabular cups/liners, etc. In an exemplary embodiment, the articulation component may be a femoral head.

As still another alternative, the silicon oxynitride materials disclosed herein may be used as a filler or otherwise incorporated into other materials, such as glasses, metals, ceramics, polymers, and the like. For example, in some embodiments, one or more of the ceramic materials disclosed herein may be used as a filler in a polymeric material. Conversely, the ceramic material disclosed herein could be used as a porous matrix to incorporate polymeric materials, glasses, or metals.

In alternative embodiments and implementations, the surface chemistry of a silicon oxynitride material may be altered to improve the wear performance characteristics of such implants. In some such implementations, the chemistry of the surface of a monolithic device or coating on a silicon oxynitride implant, silicon oxynitride coated implant, or other implantable biomedical implant, may be modified to improve wear performance characteristics. These methods for altering the surface chemistry may be employed as an alternative to, or in addition to, other methods described herein, such as methods for changing the surface roughness of an implant and/or applying a suitable coating to a biomedical implant. These methods for altering the surface chemistry may also be accomplished in several ways, as further described below.

(II) Methods of Preparing Silicon Oxynitride Materials

Another aspect of the present disclosure encompasses a process for preparing a silicon oxynitride material comprising forming a silicon nitride material block and oxidizing the silicon nitride material block. The method may produce a silicon oxynitride implant with improved wear performance.

Each of the steps of the method is detailed below.

(a) Silicon Nitride

In general, the silicon nitride may be made out of silicon nitride ceramic or doped silicon nitride ceramic substrate. Alternatively, such embodiments may comprise a silicon nitride or doped silicon nitride coating on a substrate of a different material. In other embodiments, an implant and the coating may be made up of a silicon nitride material. In still other embodiments, one or more portions or regions of an implant may include a silicon nitride material and/or a silicon nitride coating, and other portions or regions may include other biomedical materials.

Silicon nitride ceramics have tremendous flexural strength and fracture toughness. In some embodiments, such ceramics have been found to have a flexural strength greater than about 700 Mega-Pascal (MPa). Indeed, in some embodiments, the flexural strength of such ceramics have been measured at greater than about 800 MPa, greater than about 900 MPa, or about 1,000 MPa. The fracture toughness of silicon nitride ceramics in some embodiments exceeds about 7 Mega-Pascal root meter ($MPa \cdot m^{1/2}$).) Indeed, the fracture toughness of such materials in some embodiments is about 7-10 $MPa \cdot m^{1/2}$.

Examples of suitable silicon nitride materials are described in, for example, U.S. Pat. No. 6,881,229, titled "Metal-Ceramic Composite Articulation," which is incorporated by reference herein. In some embodiments, dopants such as alumina ($Al_2O_3$), yttria ($Y_2O_3$), magnesium oxide (MgO), and strontium oxide (SrO), can be processed to form a doped composition of silicon nitride. In embodiments comprising a doped silicon nitride or another similar ceramic material, the dopant amount may be optimized to achieve the highest density, mechanical, and/or antibacterial properties. In further embodiments, the biocompatible ceramic may have a flexural strength greater than about 900 MPa, and a toughness greater than about 9 $MPa \cdot m^{1/2}$. Flexural strength can be measured on standard 3-point bend specimens per American Society for Testing of Metals (ASTM) protocol method C-1161, and fracture toughness can be measured using single edge notched beam specimens per ASTM protocol method E399. In some embodiments, powders of silicon nitride may be used to form the ceramic implants, either alone or in combination with one or more of the dopants referenced above.

Other examples of suitable silicon nitride materials are described in U.S. Pat. No. 7,666,229 titled "Ceramic-Ceramic Articulation Surface Implants," which is hereby incorporated by reference. Still other examples of suitable silicon nitride materials are described in U.S. Pat. No. 7,695,521 titled "Hip Prosthesis with Monoblock Ceramic Acetabular Cup," which is also hereby incorporated by reference.

(i) Method of Preparing the Silicon Nitride Material Block

In an embodiment, preparing the silicon nitride material block may comprise preparing a slurry, where the slurry may comprise silicon, oxygen, and nitrogen, and may further comprise at least one of yttrium oxide and aluminum oxide.

The slurry may be milled to break up soft agglomerates and facilitate constituent mixing. In general, the slurry may be milled using techniques know to those of skill in the art. In an exemplary embodiment, the slurry is ball milled. Additionally, those of skill in the art would be able to determine the appropriate media, media size, and duration for the milling process.

The slurry may be dried to obtain a dried slurry, after which the dried slurry may be formed into a number of different shapes for femoral heads, articulation components, or the like. In general, the slurry may be dried using techniques known to those of skill in the art. In an exemplary embodiment, the slurry is dried using spray drying.

In general, the silicon nitride material block may be applied to biomedical components or formed or shaped into a biomedical implant. In one example, the silicon nitride material block may be formed or shaped into an articulation component. Examples of articulation components may be, without limit, femoral heads, femoral condyles, acetabular cups, etc. In an exemplary embodiment, the articulation component may be a femoral head.

In other embodiments, the silicon nitride material block may be applied to any number and type of biomedical components including, without limit, spinal cages, orthopedic screws, plates, wires, and other fixation devices, articulation devices in the spine, hip, knee, shoulder, ankle and phalanges, catheters, artificial blood vessels and shunts, implants for facial or other reconstructive plastic surgery, middle ear implants, dental devices, and the like. In an example, the silicon nitride material block may be applied to a prosthetic joint, such as a femoral head of a THA prosthesis.

Applying the silicon nitride material block to biomedical components may be performed by methods readily known by those of skill in the art.

The forming or shaping the silicon nitride material block may be performed by methods readily known by those of skill in the art. In an exemplary embodiment, the directed slurry may be consolidated using uniaxial or isostatic compacting equipment to form appropriate shapes. These shapes may then be subsequently machined to pre-fired dimensions using conventions computer-numerically-controlled (CNC) turning or milling machinery. In some embodiments, the silicon nitride material block may be formed into any number and type of biomedical components including, without limit, spinal cages, orthopedic screws, plates, wires, and other fixation devices, articulation devices in the spine, hip, knee, shoulder, ankle and phalanges, catheters, artificial blood vessels and shunts, implants for facial or other reconstructive plastic surgery, middle ear implants, dental devices, and the like. In an example, the silicon nitride material block may be applied to a prosthetic joint, such as a femoral head of a THA prosthesis.

The appropriately shaped liners or components may then be subjected to a series of heat-treatment operations including, without limit, bisque firing, sintering, and hot-isostatic pressuring.

The heat-treated liners or components may then be subjected to diamond grinding and polishing to achieve the final size and surface finish.

(b) Oxidation Methods

The surface of the silicon nitride material may be oxidized by thermal, hydrothermal, or chemical oxidation. In general, the oxidation methods descried herein convert some of the $Si_3N_4$ to $SiO_2$ on the surface of the materials.

(i) Thermal Oxidation

In general, the surface of the silicon nitride material may be oxidized using thermal oxidation. The thermal oxidation process may be conducted using means known to those of skill in the art.

In general, the thermal oxidation process may be conducted at a temperature of up to about 1100° C. In preferred embodiments, the thermal oxidation process may be conducted a temperature ranging from about 800 to about 1100° C.

The thermal oxidation process may be conducted for a duration ranging from about 5 hours to about 20 hours. In some embodiments, the thermal oxidation process may be conducted for about 5, about 6, about 7, about 8, about 9, about 10, about 11, about 12, about 13, about 14, about 15, about 16, about 17, about 18, about 19, or about 20 hours.

(ii) Hydrothermal Oxidation

In general, the surface of the silicon nitride material may be oxidized using hydrothermal oxidation. The hydrothermal oxidation process may be conducted using means known to those of skill in the art. In an exemplary embodiment, the hydrothermal oxidation may be performed in a steam autoclave. The effects of hydrothermal oxidation process on the surface chemistry of $Si_3N_4$ ceramics is illustrated in FIG. 1A (prior to hydrothermal oxidation) and FIG. 1B (after hydrothermal oxidation).

In general, the hydrothermal oxidation process may be conducted at pressures ranging from about 1 atmosphere to about 250 atmospheres. In further, embodiments, the hydrothermal oxidation process may be conducted at a pressure of about 1, about 2, about 3, about 4 about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, or about 250 atmospheres. In an exemplary embodiment, the hydrothermal oxidation process may be conducted at a pressure of about 2 atmospheres.

The hydrothermal oxidation process may be conducted for a duration ranging from about 50 to about 200 hours. In some embodiments, the hydrothermal oxidation may be conducted for about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, or about 200 hours. In an exemplary embodiment, the hydrothermal oxidation process may be conducted for a duration ranging from about 70 to about 150 hours.

The hydrothermal oxidation process may be conducted a temperature ranging from about 100° C. to about 150° C. In some embodiments, the hydrothermal oxidation may be conducted at about 100, about 105, about 110, about 115, about 120, about 125, about 130, about 135, about 140, about 145, or about 150° C. In preferred embodiments, the hydrothermal oxidation may be conducted from about 120° C. to about 135° C. In further embodiments, the hydrothermal oxidation may be conducted at about 120, about 121, about 122, about 123, about 124, about 125, about 126, about 127, about 128, about 129, about 130, about 131, about 132, about 133, about 134, or about 135° C.

(iii) Chemical Oxidation

In general, the surface of the silicon nitride material may be oxidized using chemical oxidation. The chemical oxidation process may be conducted using means know to those of skill in the art.

The chemical oxidation process may be conducted by exposing the silicon nitride material to caustic solutions. The caustic solutions may include, without limit, sodium hydroxide, ammonium hydroxide, calcium hydroxide, etc. and combinations thereof.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Preparation of Biocompatible Silicon Nitride Ceramic Components

α-$Si_3N_4$ (90 wt. %), yttrium oxide ($Y_2O_3$, 6 wt. %), and aluminum oxide ($Al_2O_3$, 4 wt. %) raw powders were admixed in water, milled, and spray dried. The spray dried powders were then consolidated using uniaxial or isostatic compacting equipment (up to 310 MPa) to form appropriate shapes, i.e., femoral heads and mechanical test-bars. These components were subsequently machined to pre-fired dimensions using conventional computer-numerically-controlled (CNC) turning or milling machinery. They were then subjected to a series of heat-treatment operations including bisque firing, sintering, and hot-isostatic pressing at temperatures up to 1700° C. The firing steps eliminated carbonaceous compounds and water, reacted the constituent raw materials, and densified the ceramic to near-final size. Diamond grinding and polishing were then performed to achieve final size and surface finish for the components.

Example 2: Oxidation of Biocompatible Silicon Nitride Ceramic Components

The final components from Example 1 were subjected to hydrothermal oxidation using a steam autoclave at a pressure of 2 atm and a temperature of 121° C. for 24, 48, or 72 hours.

Figure 2B:
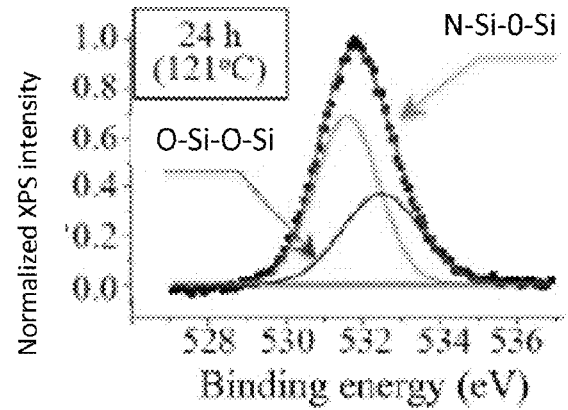
Figure 2C:
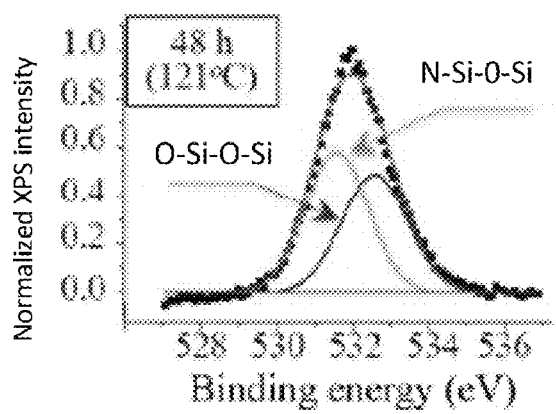
Figure 2D:
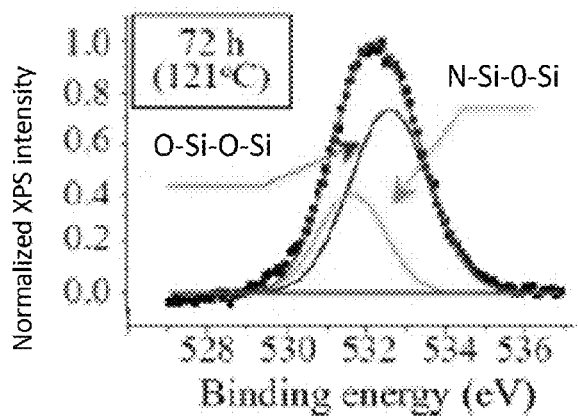
Figure 2E:
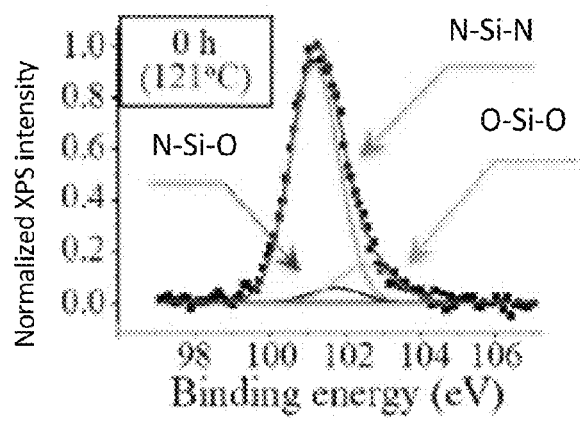
Figure 2F:
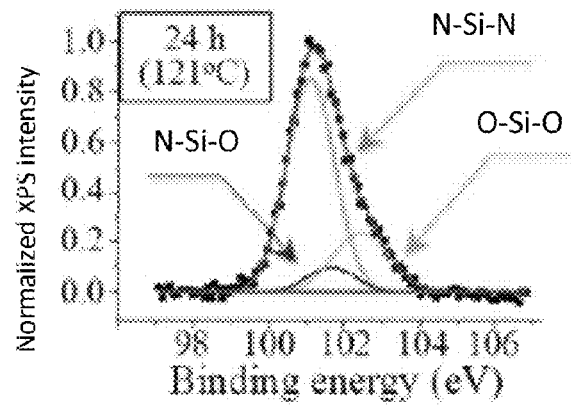
Figure 2G:
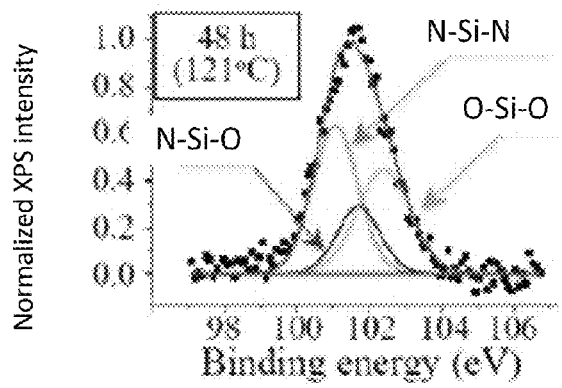
Figure 2H:
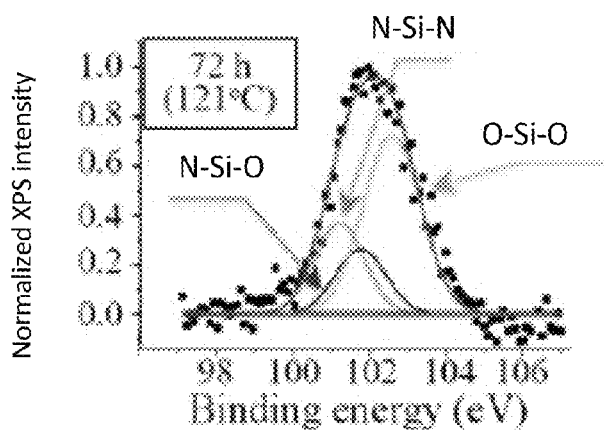

To determine the extent of the oxidation reaction, x-ray photoelectron spectroscopy was conducted on the oxidized components following 0 (FIG. 2A and FIG. 2E), 24 (FIG. 2B and FIG. 2F), 48 (FIG. 2C and FIG. 2G), and 72 (FIG. 2D and FIG. 2H) hours of exposure to the hydrothermal oxidation process. Further, the x-ray photoelectron spectroscopy analyzed the deconvolution of the O1s and $Si_2P$ bands. The results of the deconvolution of the O1s band (FIG. 2E, FIG. 2F, FIG. 2G, and FIG. 2H) demonstrated a reduction of near-surface N—Si—O—Si bonds in favor of O—Si—O—Si bonds. The results of the deconvolution of the Si2P band (FIG. 2E, FIG. 2F, FIG. 2G, and FIG. 2H) demonstrated a reduction of surface N—Si—N bonds in favor of N—Si—O and O—Si—O bonds. Both the deconvolution of the O1s band (FIG. 2A, FIG. 2B, FIG. 2C, and FIG. 2D) and $Si_2P$ band (FIG. 2E, FIG. 2F, FIG. 2G, and FIG. 2H) indicated an increase in oxidation of the $Si_3N_4$ surface.

Figure 3A:
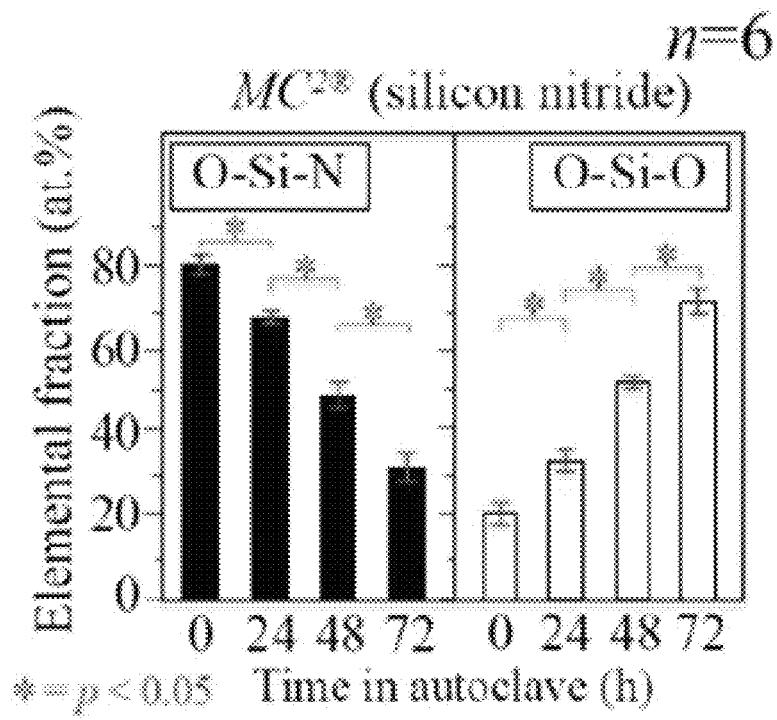
FIG. 3A and FIG. 3B depict graphs showing statistical analysis and significance of XPS data.
Figure 3B:
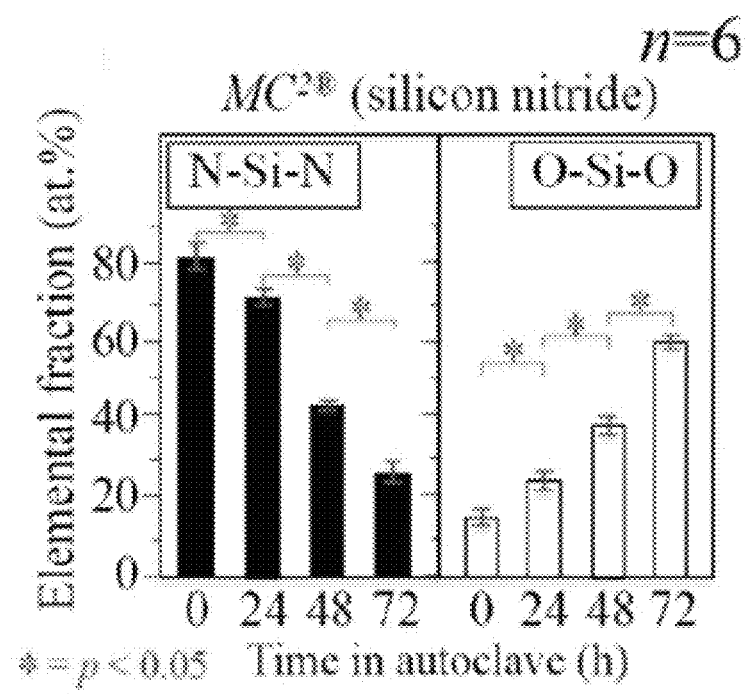
Figure 4A:
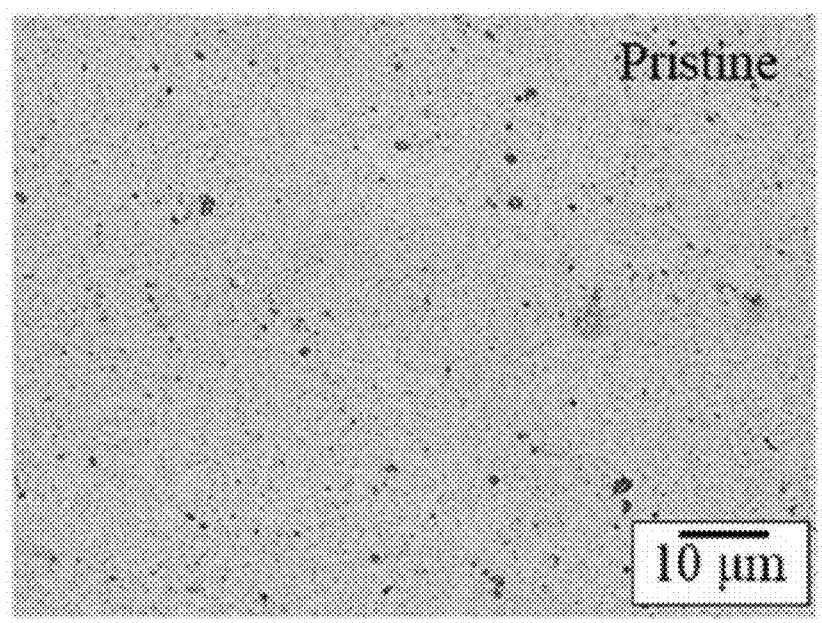
FIG. 4A and FIG. 4B depict microstructural photographs of polished $Si_3N_4$ surfaces before (i.e., pristine, FIG. 4A) and after (i.e., oxidized, FIG. 4B) a 72 hour hydrothermal treatment demonstrating that the treatment fills in the pores or voids in the ceramic surface.
Figure 4B:
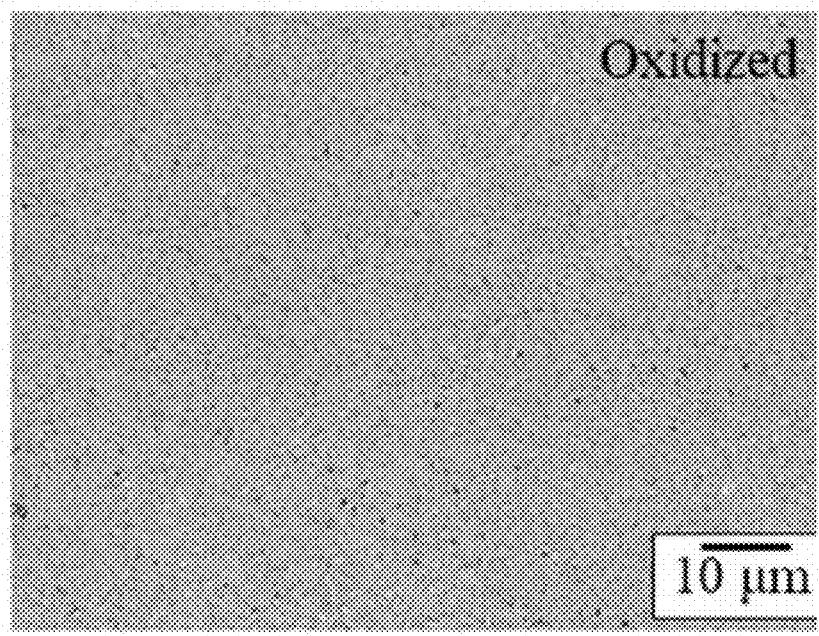

The statistical significance associated with these chemical bond changes is shown in FIG. 3A and FIG. 3B. The O1s band shows a reduction of O—Si—N bonds in favor of O—Si—O bonds (FIG. 3A). The $Si_2P$ band shows a reduction in N—Si—N bonds in favor of O—Si—O bonds (FIG. 3B). These data indicate that increasing exposure to the hydrothermal environment slowly converts $Si_3N_4$ from a mixed nitride-oxide surface to predominately an oxide condition. This is demonstrated by the microstructural photos provided in FIG. 4A and FIG. 4B. They show a pristine polished sample prior to hydrothermal treatment (FIG. 4A). The pristine surface has periodic pits and defects that are filled with a silica (i.e., $SiO_2$) glass after its hydrothermal oxidation treatment (FIG. 4B). Without being bound by theory, it is thought that engineering of this unique surface chemistry enables $Si_3N_4$ to serve as a superior articulation member in total joint arthroplasty prostheses.

Example 3: Wear Testing

Femoral heads prepared as described in Examples 1 and 2 and femoral heads prepared with BIOLOX delta (zirconia-toughened alumina) were subjected to wear testing using a hip joint simulator. Specifically, the acetabular cups were subjected to hydrothermal oxidation treatment for 72 hours at 121° C. Briefly, the acetabular cups were weighted and pre-soaked in a bath comprising bovine serum to achieve a steady level of fluid sorption (as recommended in ISO 14242/2). After 50 hours of soaking, all acetabular cups were cleaned and re-weighted. This procedure was repeated until the incremental change of the acetabular cups over 24 hours was less than 10% of the previous cumulative mass change (as part ISO 14242—Part 2).

The acetabular cups were coupled to femoral heads and tested on a 12-station hip joint simulator using a lubricant (25% sterile calf serum (Sigma Aldrich, St. Louis, MO) balanced with deionized water, 0.2% sodium azide, and 20 mmol/$dm^3$ ethylenediaminetetraacetic acid (EDTA)). After every 400,000 cycles in the hip joint simulator, the weight loss of the acetabular cups was accessed. At each weight-stop the acetabular cups were removed and cleaned using a dedicated detergent, i.e., Clean 65, at 40° C. for 15 minutes in an ultrasound washer. After rinsing, the acetabular cups were cleaned in an ultrasound washer comprising deionized water for an additional 15 minutes. The acetabular cups were initially dried using nitrogen and then placed under vacuum (0.1 bar) for 40 minutes to complete the drying. Weight loss was measured using a microbalance. Each acetabular cup was weighted three times and the average was computed.

Figure 5:
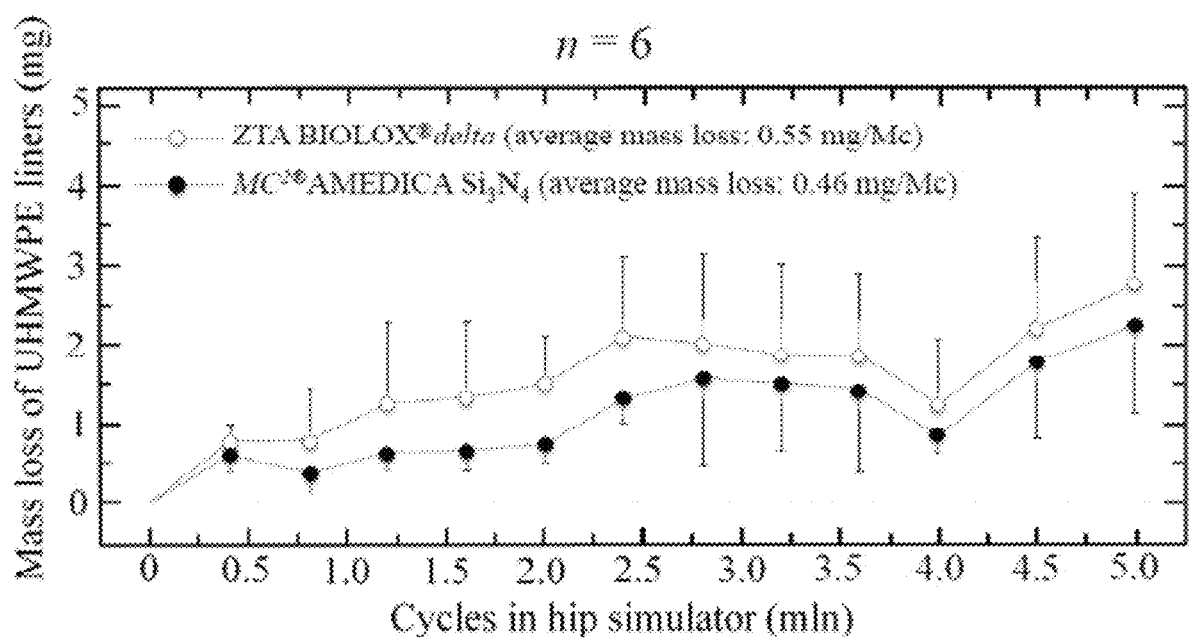
FIG. 5 depicts a graph illustrating polyethylene wear results from a standard hip simulator study comparing $MC^2$® $Si_3N_4$ to BIOLOX® delta (ZTA).

The weight loss vs. the number of cycles for the acetabular cups coupled with the femoral heads is shown in FIG. 5. The Femoral heads prepared as described in Examples 1 and 2 (labeled $MC^2$® AMEDICA $Si_3N_4$ in FIG. 5) had a lower average mass loss (0.46 mg/Mc) than the average mass loss of the ZTA BIOLOX® delta (0.55 mg/Mc).

Example 4: Static Hydrothermal Exposure

Femoral heads, prepared as described in Examples 1 and 2 and BIOLOX delta were subjected to wear testing using a hip joint simulator in a similar fashion to Example 3. However, the femoral heads were articulated against E1 (a vitamin E infused polyethylene).

Figure 6A:
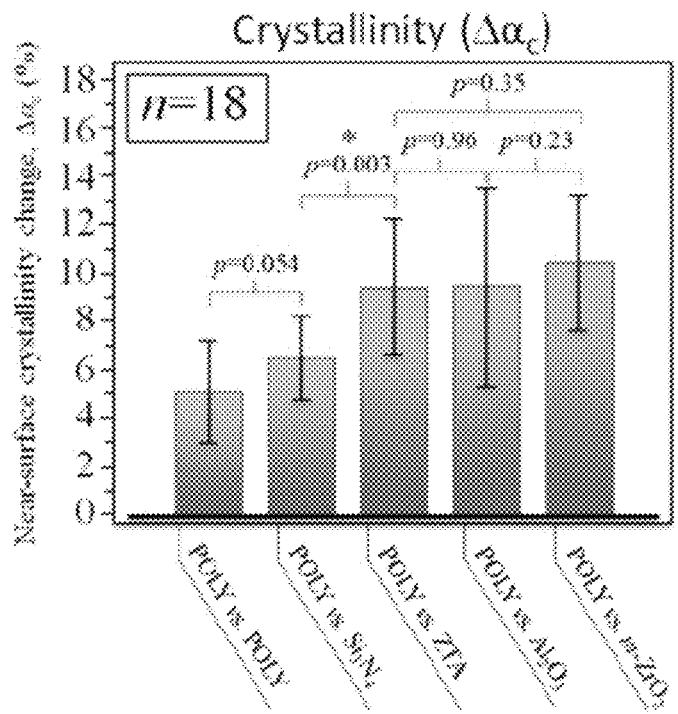
FIG. 6A and FIG. 6B depict graphs showing Raman spectroscopy measurements of crystallinity and oxidation for vitamin E doped polyethylene liners articulating against either $Si_3N_4$ or ZTA femoral heads for both non-wear-(NWZ) and main-wear-zones (MWZ)
Figure 6B:
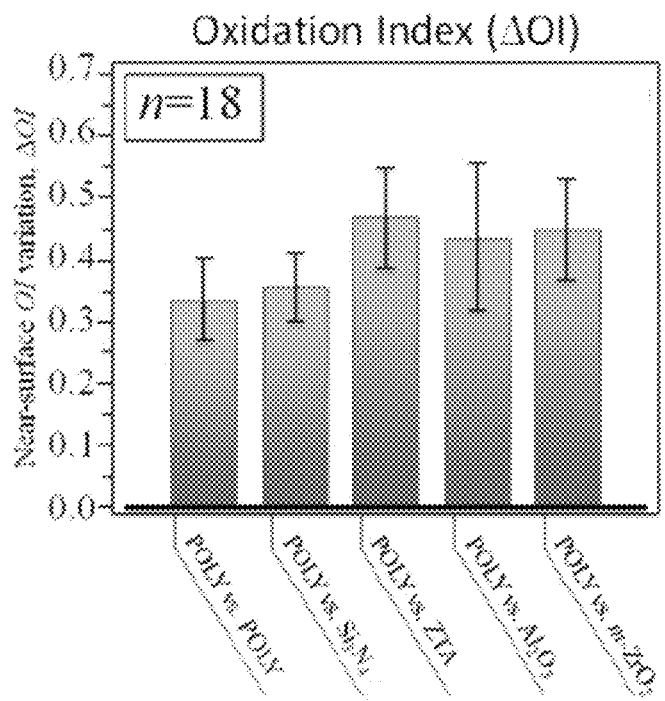

The results show the differences in the crystallinity and the corresponding oxidation indices for E1 at the sliding surface z=0) (FIG. 6A) and at a depth of 200 μm (FIG. 6B) for both the non-wear-(NWZ) and main-wear-zones (MWZ) of the liner. The $Si_3N_4$ was remarkably effective in reducing the oxidation of the liner at the surface (i.e., negative crystallinity and oxidation indices) whereas the oxidation increased for the liners articulating against ZTA. At a depth of 200 μm, the changes in crystallinity and oxidation indices for the $Si_3N_4$ remained near zero. Conversely, the liners articulating against ZTA showed marked increases in both parameters.

Example 5: Homeostatic Conditions

A block of silicon nitride ceramic as prepared in Example 1 was polished and then embedded in an acidic gel. A pH microscope (SCHEM-110; Horiba, Kyoto, Japan) capable of measuring and mapping local pH values at the surface of solids with high spatial resolution. In performing the pH mapping experiment, $Si_3N_4$ samples were fully embedded into an acidic gel consisting of artificial saliva, KCl, and agar. The pH-imaging sensor consisted of a flat semiconductor plate with a total sensing area of 2.5×2.5 cm2. The highest spatial resolution and the pH sensitivity of the sensor were 100 μm and 0.1 pH, respectively. The microscope was equipped with a light addressable potentiometric sensor, capable of detecting protons within the electrolyte. A light beam was directed from the back of the sensor with a bias voltage applied between the electrolyte and the back. Since characterization of the AC photocurrent, which was induced by the modulated illumination from the back of the sensor, depended on the amount of protons at the sensor surface, the pH value was determined to a high degree of precision by measuring the local value of electric current. The detected current signals were then converted into a color scale, with each pixel correlated to the pH image using image analysis software (Image Pro Plus, Media Cybernetics, MD, USA). This generated a visual pH map around the embedded $Si_3N_4$ samples. After embedding the test pieces, pH maps were obtained at various time intervals up to 45 min duration.

By using a pH microscope, a change in the acidity level next to the implant was noted over a period of about 45 minutes.

Figure 7:
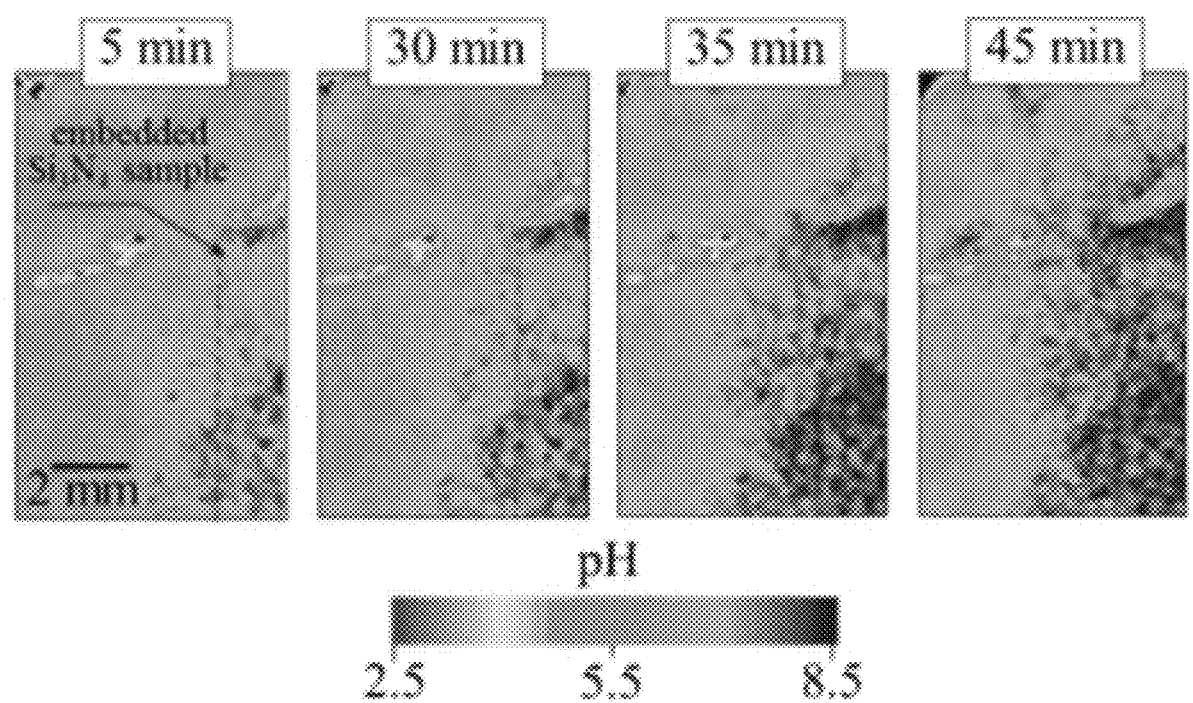
FIG. 7 depicts representative images of room-temperature evolution of pH surrounding an as-sintered (polished) $Si_3N_4$ sample as a function of time in an acidic gel. The buffering ability of $Si_3N_4$ gradually increases pH in ever wider zones of the surrounding acidic gel. The average pH of the unperturbed gel=4.5.

$Si_3N_4$ surfaces are effective in altering the local pH due to their slight dissolution and elution behavior (i.e., refer to the reactions described previously). The key results are shown in FIG. 7. This graphical diagram shows that the pH surrounding the implant immediately begins to increase from its initial acidic value of 5.5 and reaches a basic condition at ~8.5 over the 45 minute interval. The extent of the pH change can presumably be pre-engineered by altering the surface chemistry of the implant (i.e., from a mixed nitride-oxide to an oxide surface).

Example 6: Oxide Ceramic and Non-Oxide Ceramic Femoral Heads Versus UHMWPE Liners Two types of oxide femoral heads ($Al_2O_3$, BIOLOX® forte and zirconia-toughened alumina, ZTA, BIOLOX® delta, CeramTec, GmbH, Plochingen, Germany) and one type of a non-oxide femoral head ($MC^2$® $Si_3N_4$, Amedica Corporation, Salt Lake City, UT, USA) were tested versus two advanced highly crosslinked ultra-high molecular weight polyethylene liners (UHMWPE) including a sequentially irradiated and annealed material (X3, Stryker Orthopedics, Inc., Mahwah, New Jersey, USA) and a vitamin-E infused material (E1®, Zimmer Biomet, Warsaw, Indiana, USA).

Figure 8A:
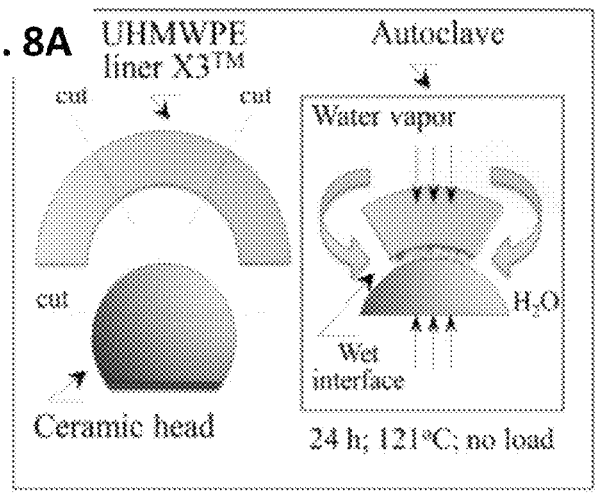
FIG. 8A is a schematic diagram of the static contact test in an autoclave used for UHMWPE/ceramic couples.
Figure 8B:
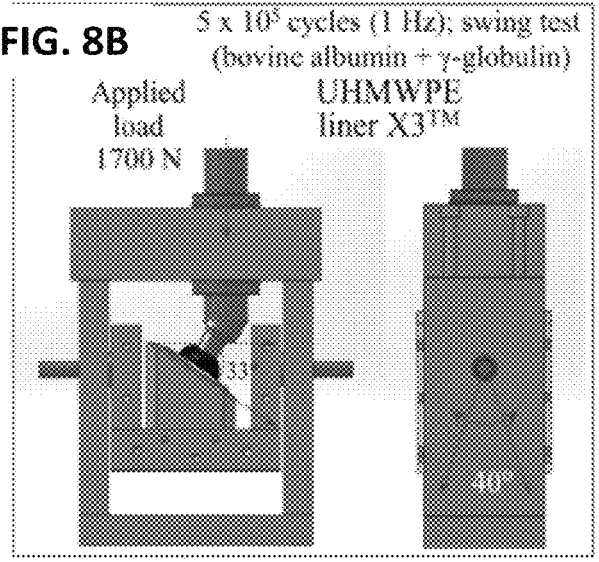
FIG. 8B illustrates the frictional swing test used for UHMWPE/ceramic couples.
Figure 8C:
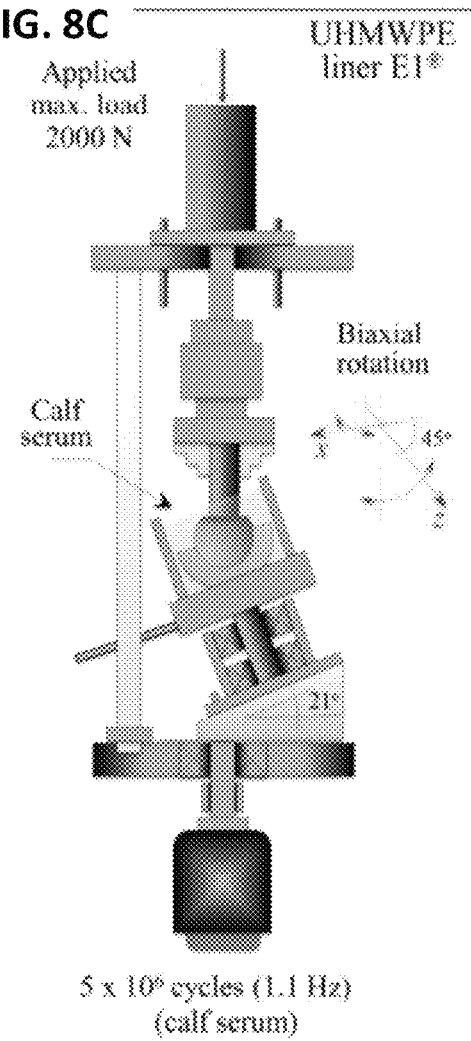
FIG. 8C illustrates a hip simulator wear test used for UHMWPE/ceramic couples.

Four experiments in total were performed: (i) A preliminary hydrothermal test in a water-vapor atmosphere as a function of time; (ii) A static, load-free, and short-term hydrothermal exposure of ceramic heads coupled with UHMWPE liners with a wet interface; (iii) A frictional reciprocating or "swing" test in lubricated environment; and, (iv) A hip simulator test with bovine serum as a lubricant. Schematic diagrams of the testing procedures in (ii), (iii), and (iv) are represented in FIGS. 8A, 8B, and 8C, respectively, with the main testing conditions given in the insets of their respective diagrams.

In the static hydrothermal test of ceramic/UHMWPE couples (item (ii) above; FIG. 8A), six X3 UHMWPE liners equal in size and shape were coupled to three types of Ø32 mm ceramic femoral heads ($Al_2O_3$, ZTA, and $Si_3N_4$). The liners had previously been gamma-ray irradiated with an average dose of 32 kGy. For comparison, six identical convex UHMWPE samples were mated and tested against six spherical (concave) UHMWPE sections. The convex UHMWPE samples were not irradiated. Lightly clamped to assure a constant contact (i.e., 25 N), the couples were subjected to accelerated an autoclave-aging test. All surfaces were dipped in pure water before being coupled and immediately placed into the autoclave at 121° C. under adiabatic water-vapor pressure. The aging time was purposely kept short at a fixed interval of 24 h, and all samples were concurrently run in the same experimental session. After the completion of the accelerated aging test, the samples were dried and cooled at a rate of 100° C./h. The test was repeated three times, using two couples for each type of material during each experimental session.

The frictional swing test (item (iii) above; FIG. 8B) was conducted using two types of Ø28 mm femoral heads (i.e., ZTA and $Si_3N_4$, n=3 each) coupled to X3 liners in a lubricated environment. The UHMWPE liners were pre-irradiated as described above. The wear testing apparatus consisted of a single station in plane reciprocating (or rocker motion) hip simulator. The simulator consisted of a stepper motor with a reducing gear, which created a swing motion of ±20 at a frequency of 1 Hz with a brief (~0.25 s) pause at +20° and −20°. The unit was placed in a compression-testing machine (600LX, Instron Corporation, Norwood, MA, USA) with a constant axial applied load of 1700 N through the entire cycle. The trunnion and liner were oriented at an angle of 33 to replicate relevant physiologic loading. Wear testing was performed at an ambient temperature (i.e., ~25 C); the temperature was periodically monitored during testing. The basic composition of the lubricant used in the test consisted of deionized water, two salts, (i.e., 8 mg/ml NaCl and 2.68 mg/ml $Na_2HPO_4.7H_2O$) and two proteins (i.e., 11.1 mg/ml bovine albumin and 5.1 mg/ml bovine γ-globulin). An addition of ~0.29 mg/ml of $FeCl_3$ to the basic lubricant was performed to replicate physiologically relevant concentrations of $Fe^{3+}$ ions (i.e., ~100 mg/l) in the joint fluid. Each test sequence was carried out to $5\times10^5$ cycles at 1 Hz.

In the hip simulator test, twelve E1®UHMWPE liners (six coupled to ZTA and six to $Si_3N_4$ femoral heads) were soaked in bovine calf serum for 4 weeks prior to wear testing to compensate for weight changes due to fluid absorption in accordance with ISO 14242-2. As shown in FIG. 8C, wear tests were performed using an inverted-position type 12-station hip joint simulator (Shore Western, Monrovia, Los Angeles, CA) in accordance with ISO 14242-3. The articulating couples were subjected to a sinusoidal load with a peak of 2 kN and a frequency of 1.1 Hz in rotation. The weight loss of the liners was measured at 0.5 million cycles (Mc) intervals using an analytical balance (Sartorius AG, Gottingen, Germany).

For comparison, two retrieved femoral heads, which had articulated against polyethylene liners in vivo were also investigated. One was a second generation monolithic $Al_2O_3$ (Biolox® Forte, CeramTec, GmbH, Plochingen, Germany). It was retrieved after 26.3 y in vivo due to wear of the polyethylene liner. The second was the so-called fourth-generation ZTA head (BIOLOX® delta, CeramTec, GmbH, Plochingen, Germany). It had been in vivo for 20 months articulating against a X3™ (Stryker Orthopedics, Inc., Mahwah, New Jersey, USA) liner and was removed due to a hip dislocation.

Example 7: Analytical Characterization

XPS analyses were performed on the surfaces of both ceramic femoral heads and UHMWPE samples described in Example 6 before and after hydrothermal aging, static hydrothermal testing of ceramic/UHMWPE couples, and frictional swing tests. A photoelectron spectrometer (JPS-9010 MC; JEOL Ltd., Tokyo, Japan) with an x-ray source of monochromatic MgKα (output 10 kV, 10 mA) was employed for these analyses. Surfaces of the samples were cleaned by $Ar^+$ sputtering in the pre-chamber, while actual measurements were conducted in the vacuum chamber at around $2\times10^{-7}$ Pa with an analyzer pass energy of 10 eV and voltage step size of 0.1 eV. X-ray incidence and takeoff angles were set at 34° and 90°, respectively. The fraction of elemental oxygen was determined by averaging three separate measurements on each of the tested UHMWPE liners at selected locations (e.g., wear zone and non-wear zone). Comparisons between the XPS outputs for ceramic and UHMWPE samples served to assess the oxygen flow between the hip joint counterparts. The sensitivity factors (in a %) used for the calculation of C, O, Si, and N were 4.079, 10.958, 2.387, and 7.039, respectively.

CL spectra were collected using a field-emission gun scanning electron microscope (FEG-SEM, SE-4300, Hitachi Co., Tokyo, Japan) equipped with an optical device. Upon electron irradiation with an acceleration voltage of 5 kV (below the threshold for perturbation of the stoichiometric structure of the investigated ceramics), the emitted CL emission was collected with an ellipsoidal mirror connected through an optical fiber bundle to a highly spectrally resolved monochromator (Triax 320, Jobin-Yvon/Horiba Group, Tokyo, Japan). A 150 g/mm grating was used throughout the experiments and a liquid nitrogen-cooled 1024×256 pixels CCD camera collected the CL emissions. The resulting spectra were analyzed with the aid of commercially available software (LabSpec 4.02, Horiba/Jobin-Yvon, Kyoto, Japan). Mapping was performed using a lateral step of 50 nm with an automatic collection of 1600 measurement points per map. The CL probe size was on the order of 68×280 nm in-depth and in-plane, respectively.

Raman assessments used a triple-monochromator (T-64000, Jobin-Ivon/Horiba Group, Kyoto, Japan) equipped with a charge-coupled device (CCD) detector. Automatic fitting algorithms for spectral de-convolution were obtained using a commercially available computational package (LabSpec 4.2, Horiba/Jobin-Yvon, Kyoto, Japan). The in-depth spatial resolution of the Raman probe was confined to ~6 μm by means of a 100× objective lens with a confocal pinhole (0100 μm) placed in the optical circuit. An automated sample stage was employed to collect square maps (50×50 $\mu m^2$ with a square mesh of 5 μm steps) of Raman spectra at different depths below the surface. Each UHMWPE sample was characterized in three separate locations before and after the accelerated aging test. Assuming that the oxidative phenomenon is the only trigger for recrystallization, variations in the oxidation index (ΔOI) were calculated using a previously calibrated phenomenological equation.

FTIR spectroscopy (FT/IR-4000 Series, Jasco, Easton, MD, USA) was used to monitor oxidation along the cross-section of the UHMWPE liners. Some of the tested liners were cut perpendicularly to the articulating surface, and a series of thin slices were obtained using a microtome device. The area of analysis was set at 100×100 $\mu m^2$. Spectra were recorded at intervals of 100 μm parallel to the free surface of the liner. The spectra were always collected in transmission mode with a spectral resolution of 4 $cm^{-1}$. The oxidation index, OI, was computed as the ratio of the area subtended by the infrared absorption bands of polyethylene located in the spectral interval 1650-1850 $cm^{-1}$ and the area of the absorption bands located in the interval 1330-1396 $cm^{-1}$ (i.e., emissions related to C—H bending). Fora limited number of samples of both types of UHMWPE liners, the OI values obtained by FTIR were compared with those obtained from Raman assessment of crystallinity variation using previously calibrated algorithms for the same materials. The FTIR and Raman comparison confirmed previous findings using these testing procedures and validated the Raman algorithms for OI assessments within a precision of ±5%.

The unpaired Student's t-test was utilized for statistical analyses. Sample sizes are stipulated in each figure's insets. A p value<0.05 was considered statistically significant and labeled with an asterisk.

Example 8: Surface Chemistry Changes Due to Hydrothermal Annealing

A preliminary procedure was designed to quantitatively assess chemical changes occurring in the oxide and non-oxide bioceramics due to hydrothermal exposure. This procedure utilized a combination of spectral data acquired by XPS and CL spectroscopy.

Figure 9A:
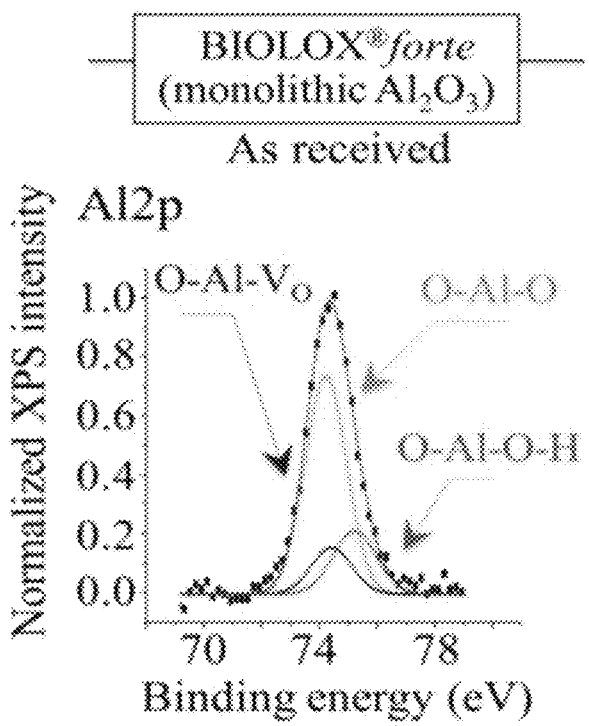
FIG. 9A shows XPS spectra and their deconvolution into sub-bands for Al2p in $Al_2O_3$(BIOLOX® forte) as received.
Figure 9B:
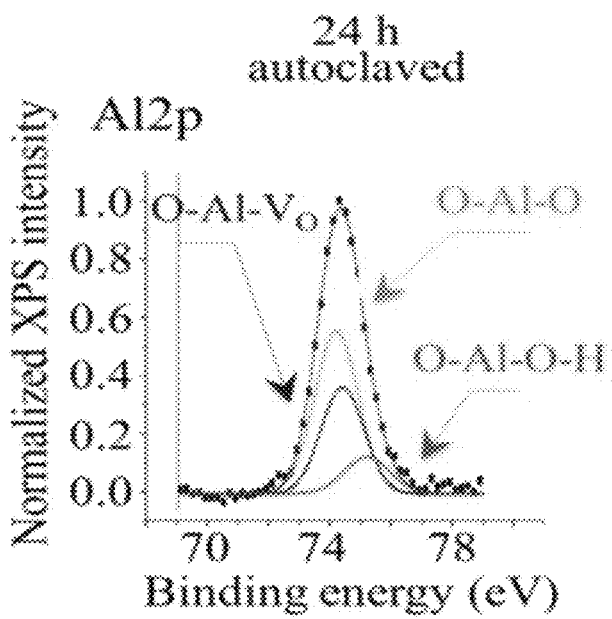
FIG. 9B shows XPS spectra and their deconvolution into sub-bands for Al2p in ZTA (BIOLOX® delta) as received.
Figure 9C:
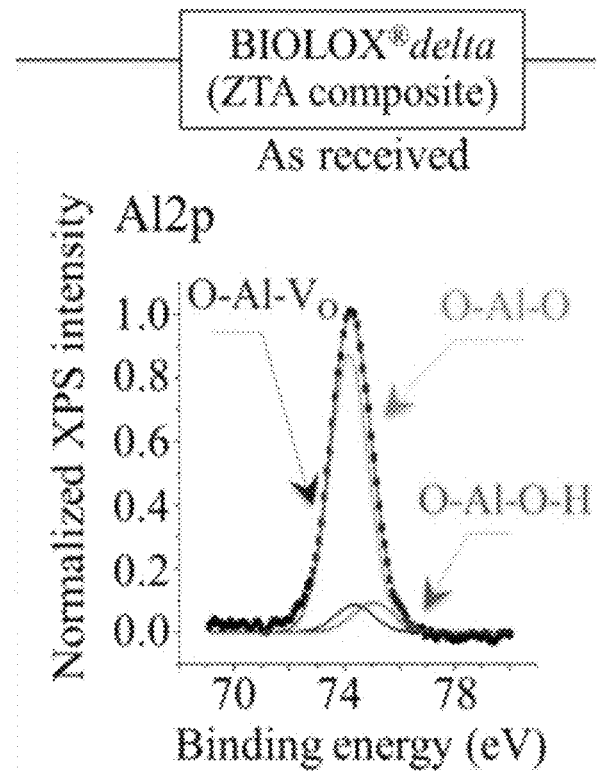
FIG. 9C shows XPS spectra and their deconvolution into sub-bands for and Si2p in $Si_3N_4$ ($MC^2$®) as received.
Figure 9D:
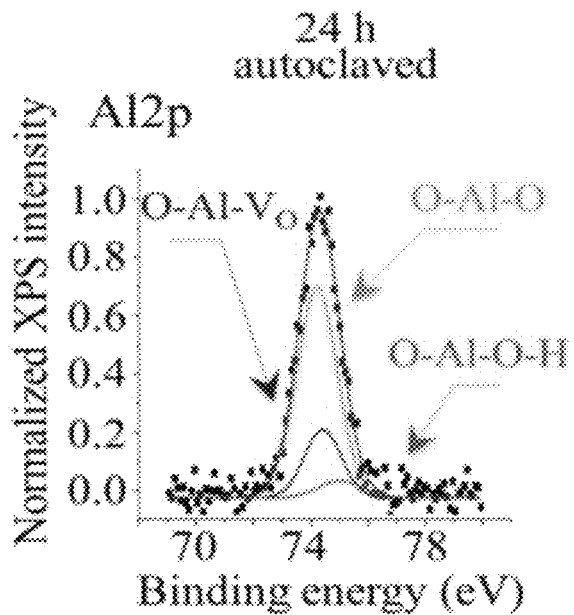
FIG. 9D shows XPS spectra and their deconvolution into sub-bands for Al2p in $Al_2O_3$(BIOLOX® forte) after 24 h adiabatic exposure in autoclave at 121° C.
Figure 9E:
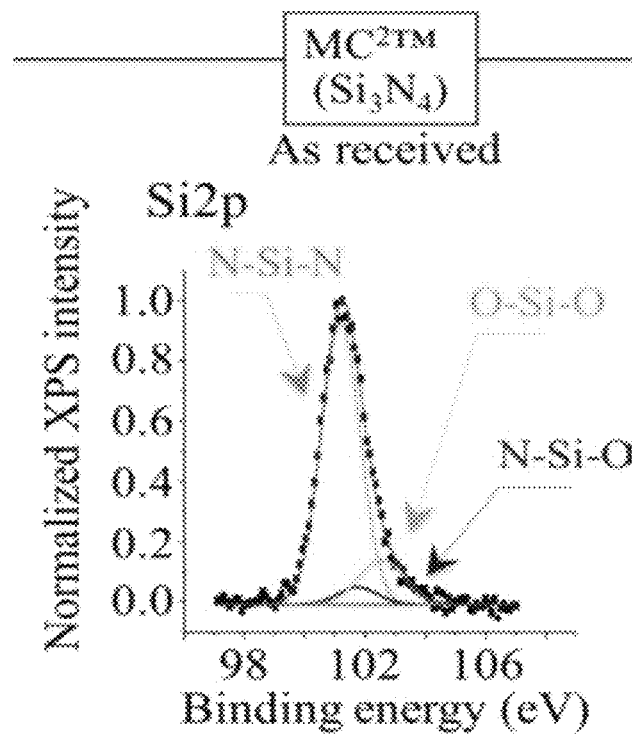
FIG. 9E shows XPS spectra and their deconvolution into sub-bands for Al2p in ZTA (BIOLOX® delta) after 24 h adiabatic exposure in autoclave at 121° C.
Figure 9F:
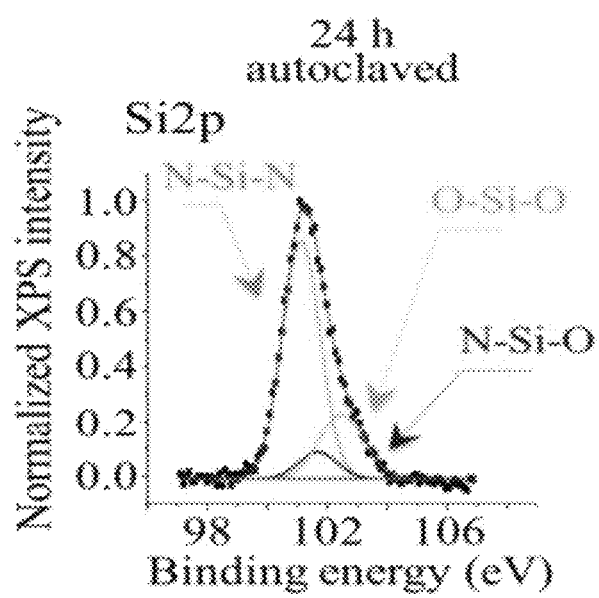
FIG. 9F shows XPS spectra and their deconvolution into sub-bands for and Si2p in $Si_3N_4$ ($MC^2$®) after 24 h adiabatic exposure in autoclave at 121° C.

FIGS. 9A, 9B, and 9C show average XPS spectra for Al2p in $Al_2O_3$(BIOLOX® forte), Al2p in ZTA (BIOLOX® delta), and Si2p in $Si_3N_4$ ($MC^2$®), respectively, as received, and FIGS. 9D, 9E and 9F show the same ceramics after 24 h adiabatic exposure in autoclave at 121° C., respectively. The oxide spectra were deconvoluted into three Voigtian sub-band components: hydroxylated (O—Al—O—H) bonds, non-hydroxylated (O—Al—O) bonds, and O—Al—VO bonds representing the bond population at the material surface. On the other hand, the non-oxide spectra included three sub-bands: one related to N—Si—N, and two additional ones from different types of Si—O bonds, namely N—Si—O and O—Si—O, which belong to the bulk $_{Si3N4}$ lattice and to a surface-formed silicon oxynitride lattice, respectively. A comparison between pristine and short-term autoclaved samples, indeed shows how quickly stoichiometric variations commonly take place at the surface of both oxide and non-oxide ceramics. In both oxide samples, the fraction of O—Al-Vo bonds increased at the expenses of both O—Al—O and O—Al—O—H bonds, while in the non-oxide sample both O—Si—O and N—Si—O types of bond underwent fractional increase at the expenses of the N—Si—N bond population.

Figure 10A:
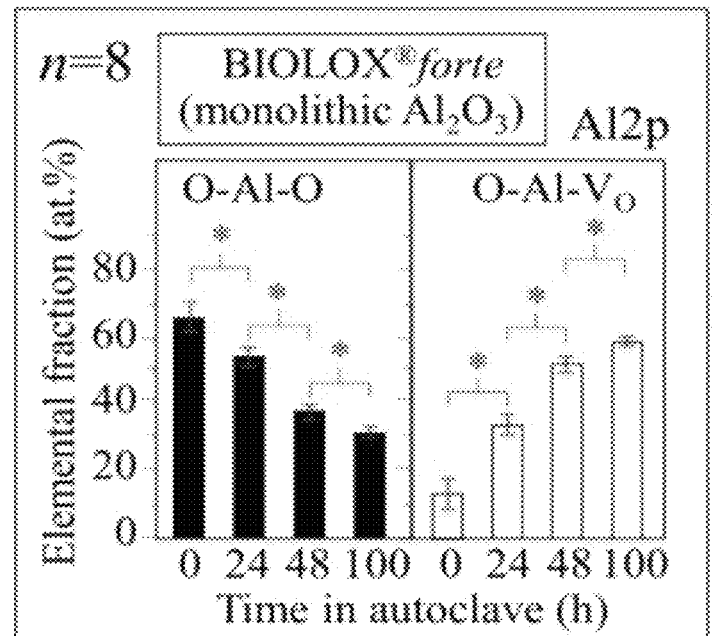
FIG. 10A shows XPS analyses as a function of autoclaving time for monolithic $Al_2O_3$(Al2p) ceramic heads.
Figure 10B:
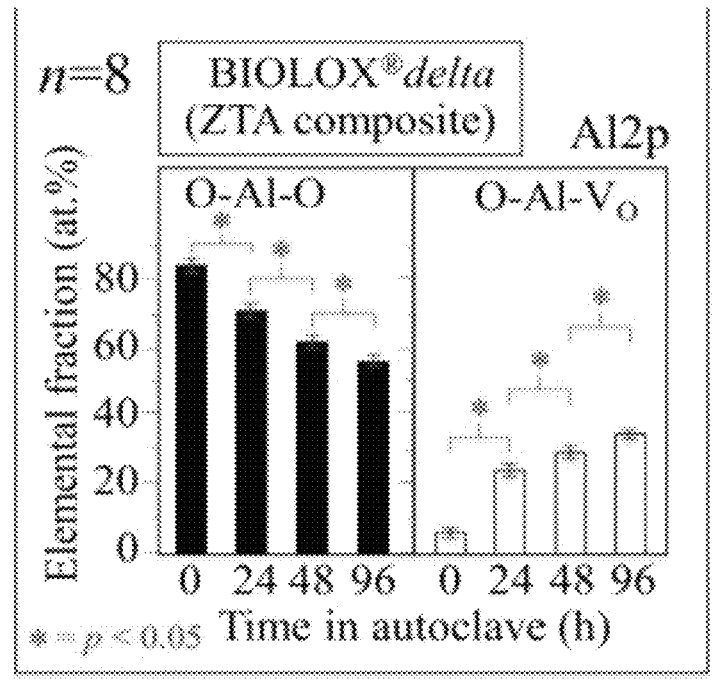
FIG. 10B shows XPS analyses as a function of autoclaving time for ZTA (Al2p) ceramic heads.

FIGS. 10A-10F show XPS results collected as a function of exposure time in the autoclave (121° C., 1 bar) by averaging n>6 measurements performed at n=6 different zones on the spherical surfaces of the ceramic heads. In FIGS. 10A and 10B, results are shown for the Al2p edge of the monolithic alumina and ZTA composite heads, respectively. The XPS spectra, fitted to the same Voigtian functions as shown in FIGS. 9A-9F, revealed homogeneous trends along with progressive reductions of O—Al—O bonds in favor of oxygen-vacancy O—Al—VO sites for both oxide ceramics (p<0.05). Closer inspection of the data showed a larger initial fraction of defective sites in the monolithic $Al_2O_3$ as compared to the composite ZTA. Also, more defects appeared in the $Al_2O_3$ with increased autoclave time than in the ZTA (cf. FIGS. 10A and 10B). Nevertheless, oxygen gradually left the surfaces of both types of oxide heads although this process occurred at different rates.

Figure 10C:
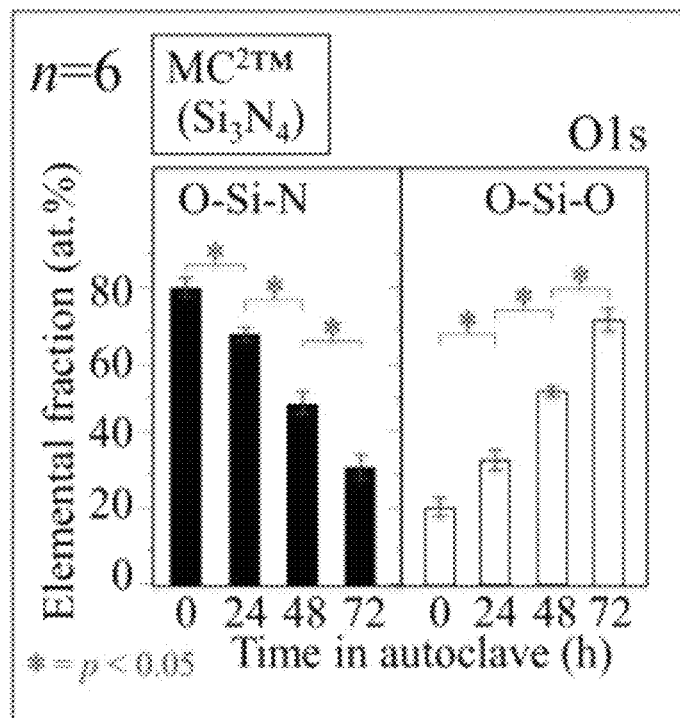
FIG. 10C shows XPS analyses as a function of autoclaving time for $Si_3N_4$ (O1s) ceramic heads.
Figure 10D:
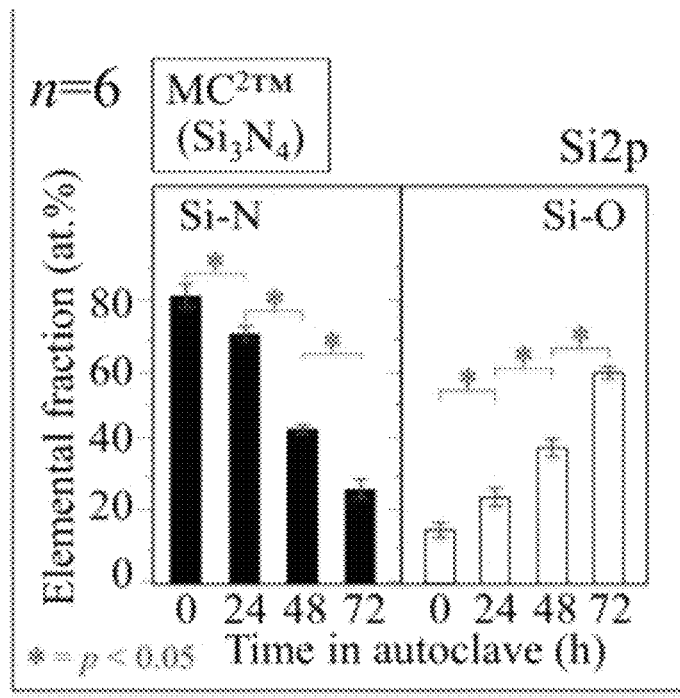
FIG. 10D shows XPS analyses as a function of autoclaving time for $Si_3N_4$ (Si2p) ceramic heads.

XPS data collected on the oxide components were then compared with values obtained under exactly the same experimental conditions for the non-oxide $Si_3N_4$ heads. FIGS. 10C and 10D show the XPS trends detected at O1s and Si2p edges for $Si_3N_4$, respectively, as a function of autoclave exposure. These latter data sets reveal the progressive fractional decrease in O—Si—N and N—Si—N bonds in favor of O—Si—O and N—Si—N sites at the ceramic's surface (p<0.05). This indicates that surface nitrogen is gradually replaced by oxygen.

Figure 11A:
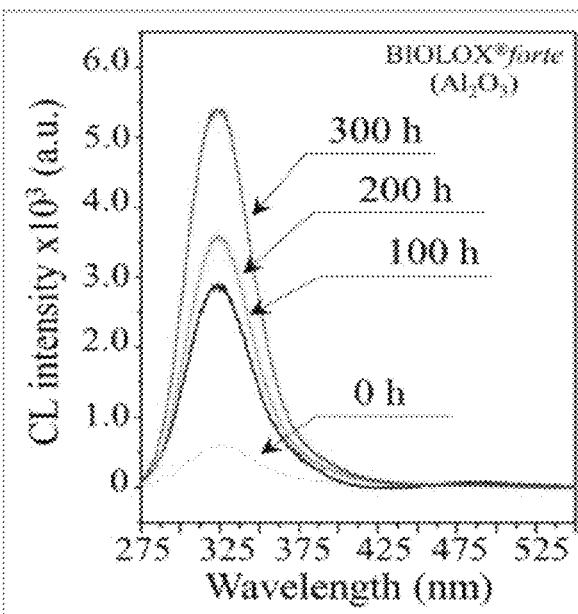
FIG. 11A shows CL analyses as a function of autoclaving time on spectral evolution in monolithic Al2O3.
Figure 11B:
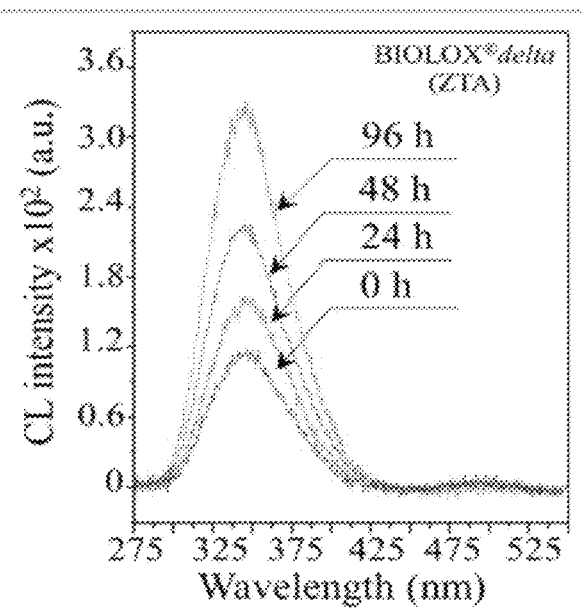
FIG. 11B shows CL analyses as a function of autoclaving time on spectral evolution in ZTA composite.
Figure 11C:
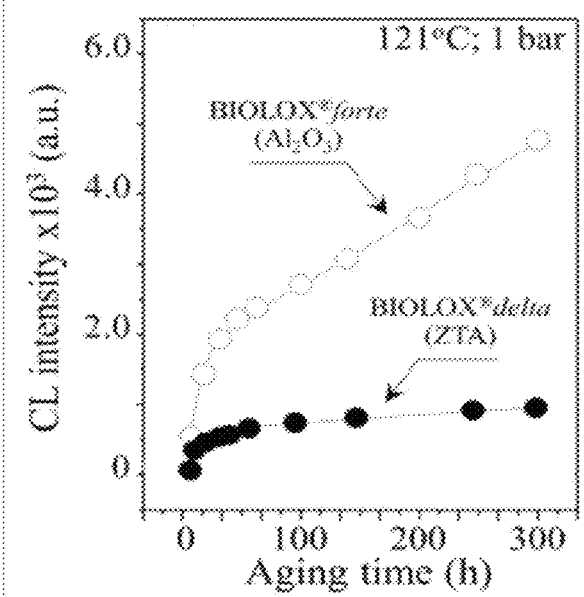
FIG. 11C plots the intensity of the CL emissions from oxygen vacancies versus autoclaving time for two types of oxide heads.
Figure 11D:
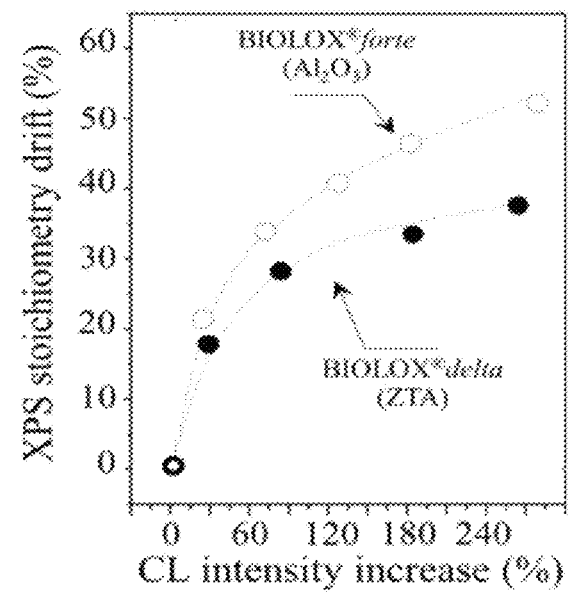
FIG. 11D shows a comparison between XPS and CL data for two types of oxide heads.

CL data for the two oxide-based ceramics are shown in FIGS. 11A-11D. FIGS. 11A and 11B show their morphological evolution of the CL spectra as a function of increasing autoclave time for femoral heads made of $Al_2O_3$ and ZTA, respectively. Both materials showed an increasing optical emission at around 325-330 nm, which corresponds to the formation of oxygen vacancies. FIG. 11C compares the CL intensity of oxygen vacancy emissions from $Al_2O_3$ and ZTA over the entire investigated autoclaving time. Consistent with the XPS data of FIGS. 10A-10D, the CL experiments revealed that the ZTA composite contained a lower initial amount of oxygen vacancies and a milder increase of their population with autoclaving time as compared to monolithic $Al_2O_3$. These differences are likely due to the presence of zirconia phase which reduced the areal fraction of oxygen-emitting alumina by ~17 vol %. Additionally, the presence of $Cr^{3+}$ (i.e., a dopant intentionally added to substitute for $Al^{3+}$) delays dehydroxylation due to its higher energy hydrogen-bonding as compared to $Al^{3+}$. Note that the geometry of the electron probe in both XPS and CL is similarly shallow (i.e., nanometer depth) which suggests that results from these two methods are comparable. FIG. 11D links drifts in stoichiometry by XPS to increases in CL intensities for both the $Al_2O_3$ and ZTA heads. These plots provide semi-quantitative data for oxygen-vacancies formed in vitro at the surfaces of these two ceramics.

Similar CL experiments were conducted on the surfaces of $Si_3N_4$ heads as a function of autoclaving time (not shown). The propensity for oxygen to replace nitrogen was reflected by an increased intensity of a CL band at ~650 nm which belongs to oxygen-excess sites (i.e., non-bridging oxygen hole centers) typical of silica glass.

FIGS. 10A-10D and 11A-11D reveal opposite scenarios for oxide and non-oxide ceramics. Adsorption of molecular water plays the role of a solvent for the oxide ceramics with free oxygen flowing away from their surfaces, whereas it is an oxidant for $Si_3N_4$ and therefore oxygen flows towards its surface. Water molecules possess different strengths upon hydrogen-bonding to the oxide and non-oxide ceramic surfaces (i.e., aluminols and silanols for $Al_2O_3$-based and $Si_3N_4$ ceramics, respectively). Strong bonds result from H-bond acceptors when silanols form and from H-bond donors at interfacial aluminols; whereas, weak bonds form from H-bond donors and acceptors at the surfaces of $Si_3N_4$ and $Al_2O_3$, respectively.

Example 9: Static Hydrothermal Test on Ceramic/Polyethylene Couples

The impact of oxygen movement on the crystallization and oxidation of the polyethylene liners when coupled to various ceramic femoral heads was initially examined using static hydrothermal-activated tests under near zero loads. Data in this Example validate preliminary Raman/FT-IR characterizations of the crystallinity and oxidation of X3 highly crosslinked polyethylene liners. Specifically, the aim of this Example was to confirm previous data using new experiments on the same brand of advanced polyethylene by adding XPS analyses of the polyethylene surfaces to the prior Raman and FTIR characterizations. XPS analyses on the ceramic surfaces were also performed, but they did not tangibly differ from the hydrothermal tests described in Example 8. Accordingly, FIGS. 10A-10D represent the results of the static hydrothermal testing of these ceramics when coupled to UHMWPE liners.

Figure 12A:
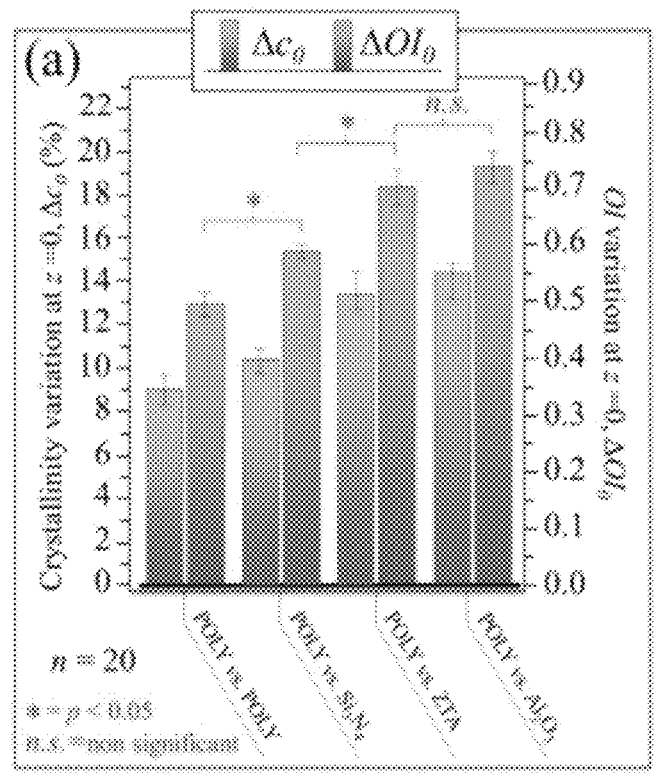
FIG. 12A shows variations of crystallinity and oxidation indices as detected by vibrational spectroscopy for X3 UHMWPE liners statically coupled to oxide and non-oxide ceramic heads for 24 h in an autoclave.
Figure 12B:
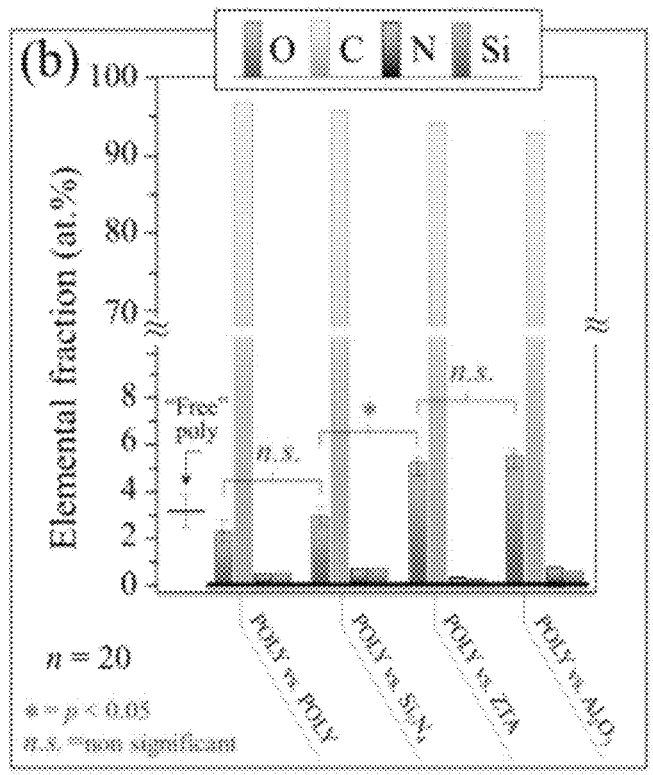
FIG. 12B shows XPS analyses of the same liners in FIG. 12A.

FIG. 12A shows crystallinity, $\Delta c_O$, and oxidation index variations, $\Delta OI_O$, at the surfaces of the X3™ polyethylene liners with respect to their pristine values. Polyethylene versus polyethylene couples (i.e., X3™ vs. X3™) with the same geometrical configuration as the ceramic versus polyethylene couples were used as positive controls. The null hypothesis was that all of the tested ceramics (if completely bioinert) would induce the same variations in $\Delta c_O$ and $\Delta OI_O$ as the all-polyethylene couples. FIG. 12B summarizes the XPS results collected at the polyethylene surface for each of the investigated couples.

Note that the data presented in FIGS. 12A and 12B clearly diverge from the null hypothesis. In the couples containing the oxide ceramics, a significant increase in surface crystallization (~55%) and oxidation (~45%) was observed. The results were statistical valid when compared to the positive control (polyethylene vs. polyethylene couples) while the difference between the two oxide-containing couples was not significant. The liners coupled to the $Si_3N_4$ heads experienced ~30% lower increase in their oxidation indices than liners coupled to the oxide ceramics; and they were only ~14% higher than the control couples. The XPS data at the liner surfaces were consistent with vibrational data. They showed the highest amount of oxygen at the surfaces of liners coupled to ceramic oxide heads (i.e., about twice the amount detected in the all-polyethylene couples), with no statistically significant difference between liners coupled to $Al_2O_3$ or ZTA. The oxygen content detected by XPS at the surfaces of the liners coupled to $Si_3N_4$ was only slightly higher (with no statistical relevance) than values detected at the surface of the control couples. Traces of N and Si were found by XPS on the surface of all tested liners; this was presumably due to annealing and polishing of the UHMWPE components, respectively, during their manufacture.

Assuming that the environmental loading on all of the samples was both geometrically and thermodynamically identical, it follows that the increase in polyethylene oxidation for the oxide ceramic couples (as compared to the controls) arises from oxygen emissions from the ceramic surfaces. This hypothesis is consistent with the XPS data for these liners (cf., FIGS. 10A and 10B and FIG. 12B). After 24 hours of exposure in the hydro-thermal environment, fractional increases of the O—Al-Vo bonds in the oxide ceramics (~50%) were nearly equal to the fractional increases in oxygen bonds detected at the surfaces of the polyethylene liners.

In an attempt to quantify the potential protective action of the $Si_3N_4$ head in preventing oxidation of the UHMWPE liner, an X3™ liner identically exposed to the hydrothermal test conditions was subsequently spectroscopically characterized (n=3). This additional sample is referred to as the "free" polyethylene. The $\Delta c_0$ and $\Delta OI_0$ values for this sample were between the polyethylene control couple and the polyethylene versus $Si_3N_4$ couple with no statistically significant differences with respect to the two couples. Regarding the oxygen content detected by XPS at the surface of the "free" sample (FIG. 12B), it was slightly higher than at the surface of the liner coupled with $Si_3N_4$, but this difference was not statistically relevant.

In summary, non-oxide ceramics clearly proved to be more friendly counterparts in delaying UHMWPE oxidation than the oxide ceramics in this specific static hydrothermal test. Although the oxygen contamination by oxide ceramics was clearly quantified, any protective effect by non-oxide ceramics in counteracting the degradation of UHMWPE liners needs to be assessed in longer-term hydrothermal experiments.

Example 10: Frictional Swing Test on Ceramic/Polyethylene Couples

An additional set of experiments was conceived based on frictional interactions between the two lubricated components of the couple under swing kinetics but left aside hydrothermal activation. The purpose of these tests was to determine the impact of different femoral head materials on the oxidation of UHMWPE (i.e., X3™) using frictional sliding under a moderate load. FIGS. 13A and 13B show typical Al2p XPS spectra from ZTA femoral heads before and after this frictional swing test for $5\times10^5$ cycles at 1 Hz with a 1700 N load under lubricated conditions, respectively. This frictional test induced significant alterations of the XPS spectrum at the surface of the oxide composite demonstrating a drift in off-stoichiometry towards an oxygen-vacancy-rich environment. A quantitative plot of the variations observed in the Al2p spectra is given in FIG. 13C. This plot reveals a ~28% decrease of the O—Al—O bond population in favor of a nearly equivalent increase of O—Al—VO bonds. The O1s edge consistently showed a decrease of Al—O—Al—O population in favor of Al—O—Al—VO while confirming surface de-hydroxylation with a significant reduction in the population of Al—O—H bonds (FIG. 13D). On the one hand, the Zr3d edge of the ZTA surface (also shown in FIG. 13D) revealed an invariant fraction of Zr—O—H and an increase in Zr—O—Zr bonds. This observation was consistent with the fact that dehydroxylation hardly occurs in $ZrO_2$ ceramics due to a much stronger O—H bond as compared to the O—H bond at the surface of $Al_2O_3$. On the other hand, its occurrence is a consequence of free oxygen from the tribolayer filling pre-existing vacancies in the metastable tetragonal (Y-doped) zirconia lattice, which in turn induces spontaneous phase transformation into the monoclinic polymorph.

FIGS. 14A and 14B represent typical N1s XPS spectra from the $Si_3N_4$ femoral heads before and after the frictional swing test, respectively. In these cases, prolonged frictional exposure induced dramatic off-stoichiometry at their surfaces with a decrease of ~27% in Si—N—Si—N bonds in favor of a nearly equivalent increase of Si—N—Si—O bonds, while the population of the Si—N—H bonds remained unaltered (cf., FIG. 14C). XPS data at the O1s edge confirmed the trend observed at the N1s edge. A reduction in N—Si—N bonds was also observed at the Si2p edge (cf., FIG. 14D). The XPS data provided in FIGS. 13A-13D and FIGS. 14A-14D demonstrated opposite trends for oxygen chemistry at the surfaces of the ZTA and $Si_3N_4$ ceramics due to their frictional loading against UHMWPE liners. The former material released oxygen from its surface (i.e., an increase of Al—O—Al—VO bonds), while the latter scavenged oxygen (i.e., an increase of Si—N—Si—O bonds).

Figures 15A, 15B:
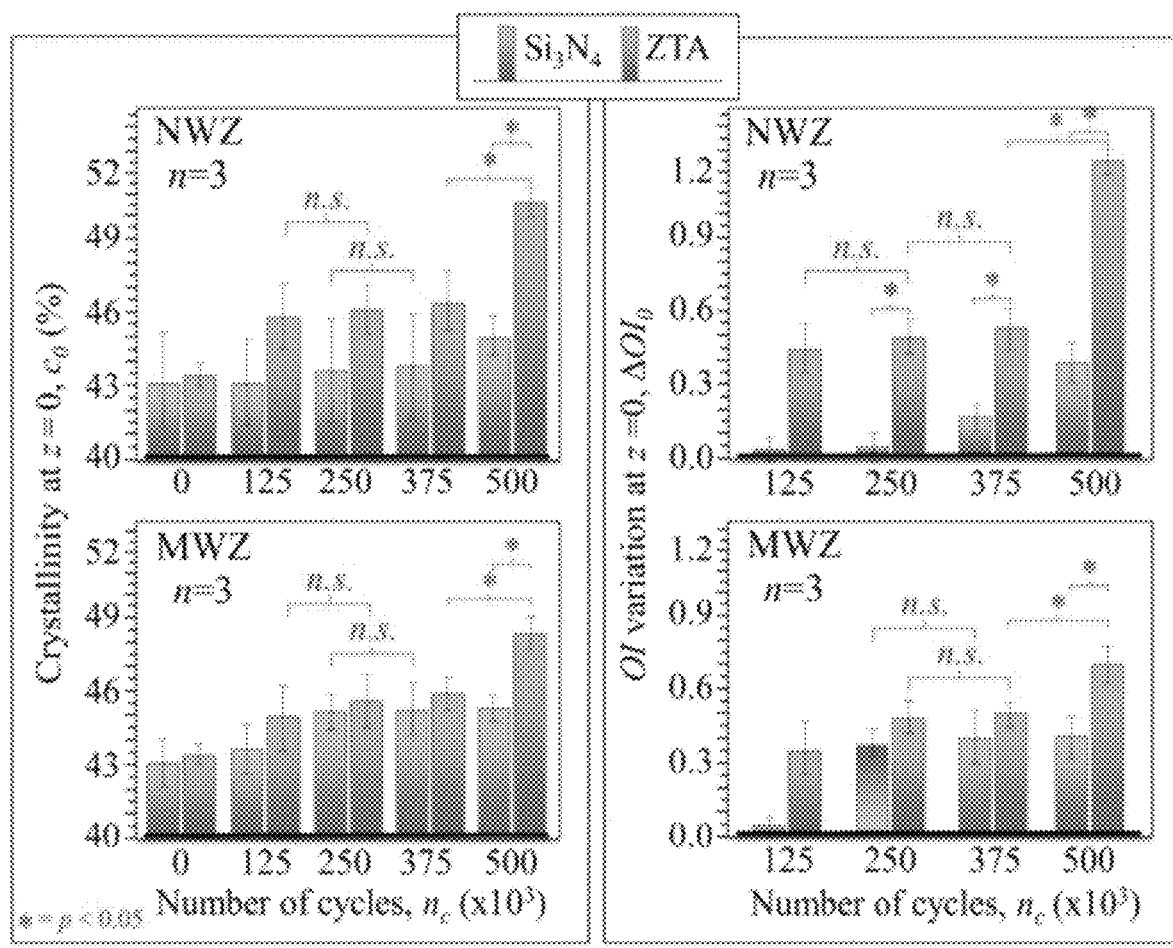
FIG. 15A shows crystallinity at the surface of X3 UHMWPE liners coupled to $Si_3N_4$ and ZTA as a function of the number of cycles, $n_c$, of frictional swing testing.
FIG. 15B shows oxidation at the surface of X3 UHMWPE liners coupled to $Si_3N_4$ and ZTA as a function of the number of cycles, $n_c$, of frictional swing testing.

In order to determine the effect this opposite movement of oxygen had on the UHMWPE liners, their vibrational behavior was monitored as a function of the number of swing cycles, $n_c$. FIGS. 15A and 15B show crystallinity and variations in oxidation indices as a function of $n_c$ for liners coupled to ZTA and silicon nitride (data are from non-wear zones, NWZ, and main-wear zones, MWZ), respectively. The results of FIGS. 15A-15B reveal that frictional contact increased surface crystallinity and oxidation indices for both NWZ and MWZ locations independent of whether the liners were coupled to oxide or non-oxide ceramic heads. However, the UHMWPE degradation was significantly greater in liners coupled to the ZTA heads, especially in the NWZ (i.e., $\Delta$OI-1.2 vs. 0.4 after $5\times10^5$ cycles) In the MWZ, the average $\Delta$OI for liners coupled to the $Si_3N_4$ heads was the same as the NWZ (i.e., ~0.4), while the liners coupled to ZTA was ~0.7 lower than the NWZ. Note that the trend in $\Delta$OI vs. $n_c$ in the MWZ tended to saturate for liners coupled to $Si_3N_4$, while it exponentially increased in the NWZ for liners coupled to both ZTA and $Si_3N_4$ ceramics. Accordingly, there are likely competing effects in the MWZ between material removal from the liner due to frictional wear and the rate of crystallization and oxidation of the UHMWPE's surfaces. The latter rate appears faster than the former. Consequently, the $\Delta$OI continuously increased with $n_c$. This appeared to be the case for the NWZ in which the material removal rate was essentially zero. Conversely, a slower oxidation rate in comparison to frictional material loss led to saturation of the $\Delta$OI vs. $n_c$ for the MWZ.

Figure 16A:
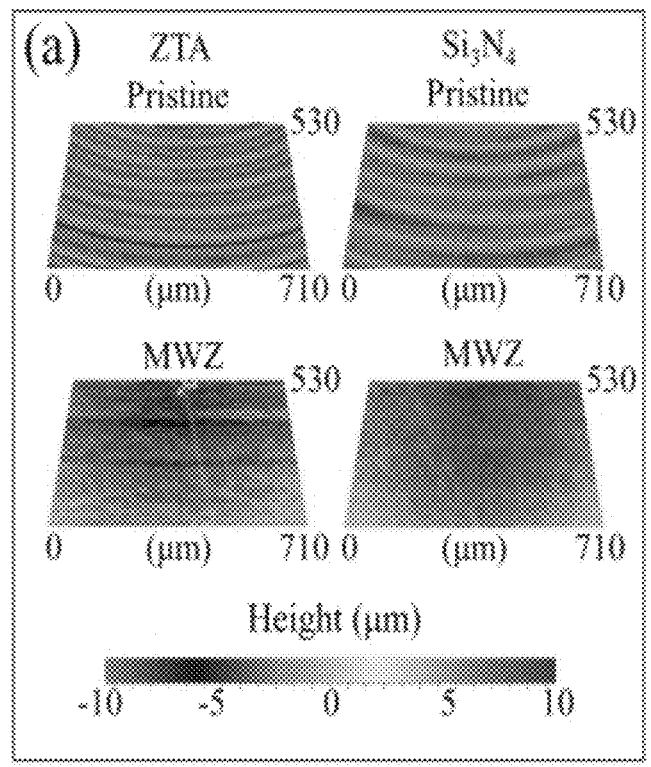
FIG. 16A shows scanning laser microscopy images of pristine and MWZ worn surfaces (after $5 \times 10^5$ swing cycles) of X3™ UHMWPE liners coupled to ZTA and $Si_3N_4$ femoral heads.
Figure 16B:
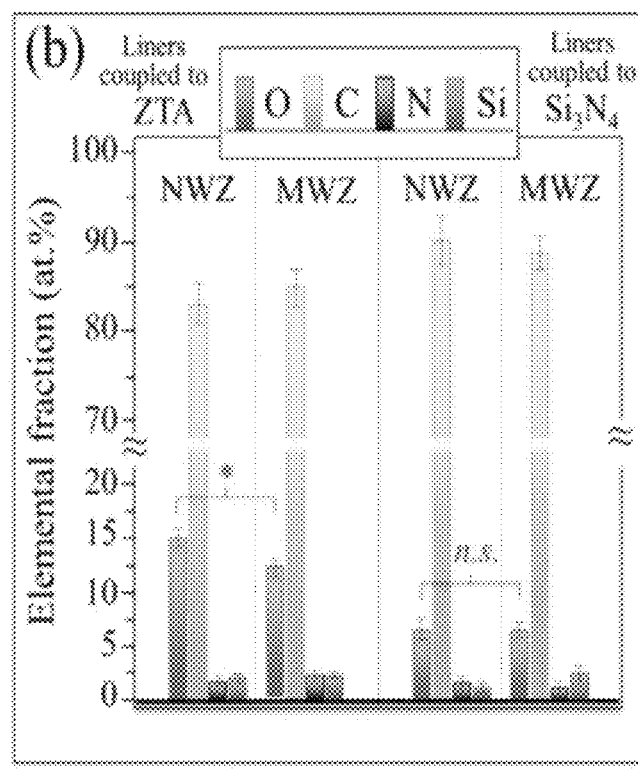
FIG. 16B shows results of XPS analyses in NWZ and MWZ of the same liners.

Based on the removal of the UHMWPE's machining marks and gravimetric analyses, wear rates for both types of couples were similar (cf., laser microscopy results of FIG. 16A and weight loss values of ~0.9 mg, respectively). FIG. 16B provides a comparison of XPS data collected at the surface of the liners in both the MWZ and NWZ at $n_c=5\times10^5$. The number of oxygen bonds at the NWZ surfaces of liners coupled to the ZTA heads was the highest in this set of experiments (~15 at %) and twofold higher than liners coupled to the $Si_3N_4$ heads. While the level of liner oxidation for $Si_3N_4$ couples was conspicuously the same for NWZ and MWZ, the ZTA couples showed higher oxidation in the NWZ as compared to MWZ (i.e., ~15 vs. 12.5 at %). This suggests that the oxidation rate for the liners coupled to ZTA was faster than the corresponding material removal rate. This level of oxidation was definitely a preponderant phenomenon for the ZTA couples, reaching OI values as high as ~1.2 in the NWZ. These frictional swing-test experiments demonstrated that the oxidation of the UHMWPE liners, particularly those coupled to the ZTA heads, was predominantly due to a chemical reaction rather than to mechanical action.

Example 11: Hip-Simulator Test of Ceramic/Polyethylene Couples

The crystallinity and oxidation of vitamin-E doped UHMWPE liners coupled to either ZTA or $Si_3N_4$ heads were evaluated after 5-million-cycles in a standard hip simulator test. This is part of an ongoing 12-million-cycle study aimed at evaluating the suitability of $Si_3N_4$ as an alternative ceramic bearing material. While anti-oxidant vitamin-E has demonstrated its ability to delay liner oxidation during in vitro experiments, the purpose of these spectroscopic tests was to determine if the coupling of vitamin-E doped UHMWPE liners to non-oxide ceramic heads could also lead to tangible advantages in terms of additional retardation of liner oxidation.

Both types of wear couples showed good performance. Average polyethylene liner wear rates were 0.55 and 0.46 mg per million cycles for the ZTA and $Si_3N_4$ couples, respectively. FIGS. 17A and 17B compare crystallinity, $\Delta c$, and oxidation index, $\Delta OI$, variations for the ZTA and $Si_3N_4$ couples at the liner's surface and at a depth of 200 μm, respectively. Similar to the frictional swing test, the UHMWPE liners coupled to ZTA had larger increases in both the amount of crystallization and the level of oxidation when compared to liners coupled to $Si_3N_4$. The microstructural degradation of the UHMWPE was more pronounced at the surface than in the depth of the ZTA coupled liners. Conversely, no crystallization was apparent for the liners coupled to $Si_3N_4$ at either of the investigated depths. This was accompanied by essentially no change in the liners oxidation index (i.e., $\Delta OI \sim 0$). In fact, a slight increase in amorphization was noted for the liners articulated against $Si_3N_4$ (FIG. 17A). Although a direct comparison between the two types of UHMWPE liners (i.e., X3 v. E1®) has yet to be made, it appears that the amount of surface oxidation associated with the E1® liners was about one order of magnitude lower than the X3 in spite of the fact that the E1® liners had ~10 times the number of testing cycles. Nevertheless, an increase in the oxidation index for the E1® liners coupled to ZTA heads was a tangible result of this Example. With 5 million cycles being kinematically equivalent to about 2.5 years in vivo, it appears that addition of vitamin-E does not completely eliminate liner oxidation in artificial hip joints coupled to oxide ceramics.

Example 12: Retrieval Analyses

This Example provides an assessment of surface off-stoichiometry due to the depletion of oxygen in oxide ceramic femoral heads retrieved from human patients. These in vivo results are contrasted to the in vitro experiments discussed in earlier Examples. Two retrieval cases are presented as typical examples of both monolithic $Al_2O_3$ and ZTA heads. Conversely, $Si_3N_4$ is a new material and has not been cleared for use in total hip arthroplasty; therefore retrievals are not yet available.

Figure 18A:
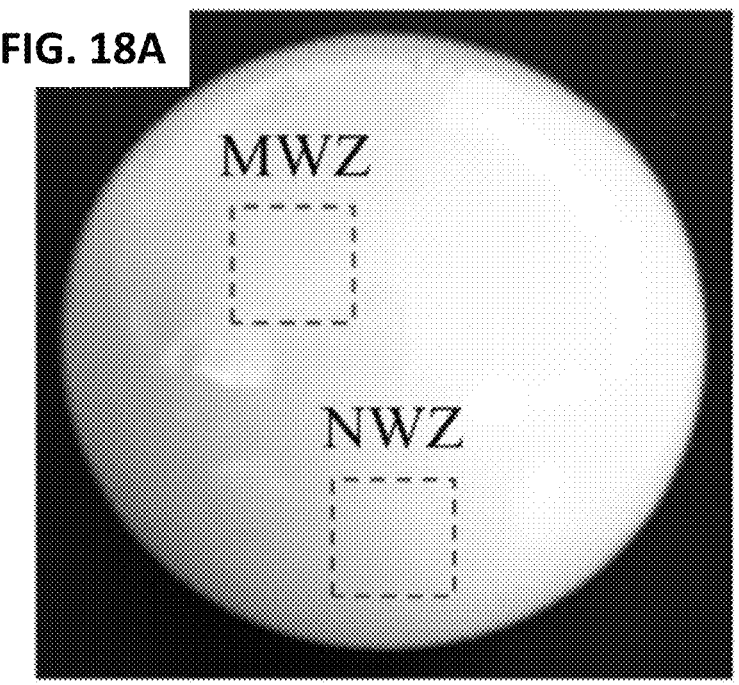
FIG. 18A shows a long-term in vivo exposed monolithic $Al_2O_3$ femoral head.
Figure 18B:
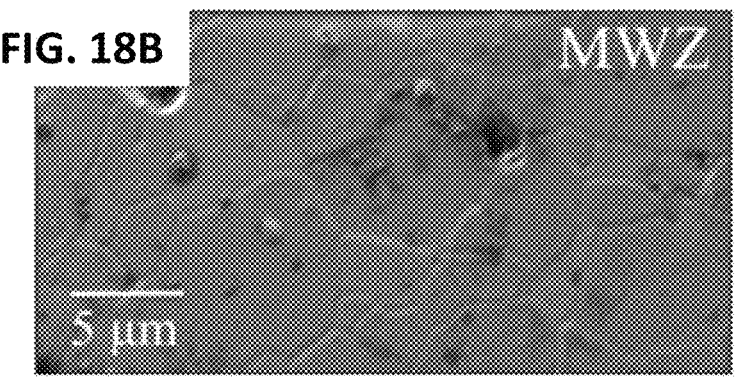
FIG. 18B shows the microstructure in the MWZ of a long-term in vivo exposed monolithic $Al_2O_3$ femoral head.
Figure 18C:
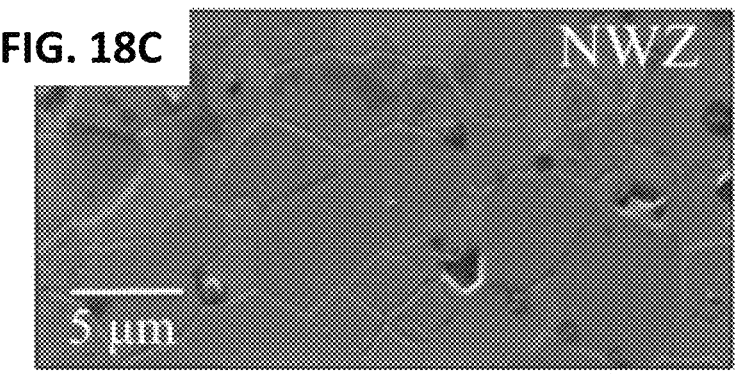
FIG. 18C shows its microstructure in the NWZ.
Figure 18D:
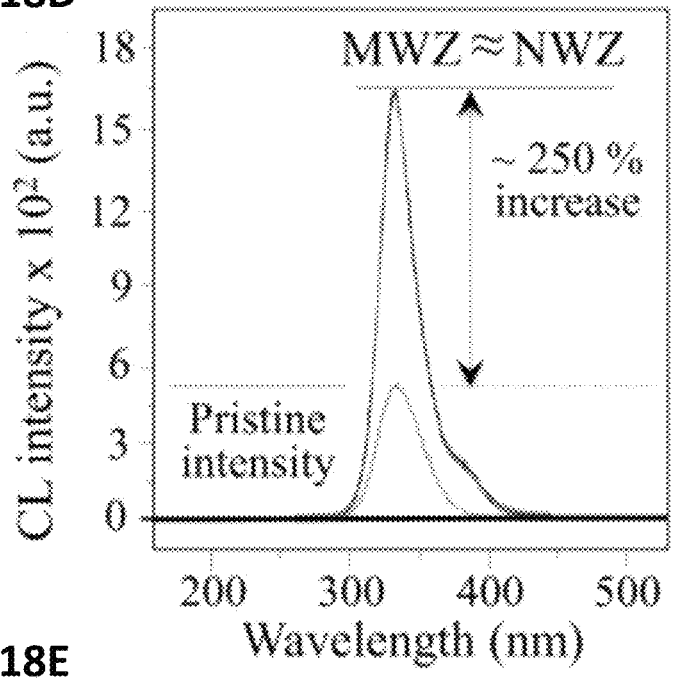
FIG. 18D shows its CL oxygen vacancy emissions compared to that of a pristine $Al_2O_3$ sample.
Figure 18E:
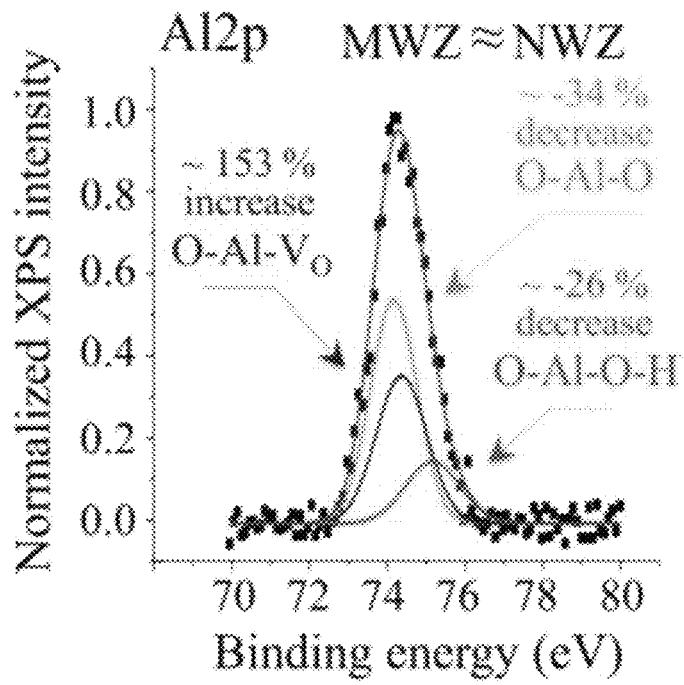
FIG. 18E shows its deconvoluted average XPS (Al2p) spectrum.

FIG. 18A shows a photograph of a femoral head from an earlier generation of monolithic $Al_2O_3$ articulating against a polyethylene liner for 26.3 years in vivo. Scanning electron micrographs of its MWZ and NWZ surfaces (FIGS. 18B and 18C, respectively) revealed a relatively coarse granular structure typical of early grades of biomedical alumina, with an average grain size ranging between 3 and 6 μm. Although grain boundaries were clearly visible—probably due to chemical etching in the acidic joint environment—no significant surface damage was observed in both the MWZ and NWZ. This result is consistent with long-term articulation against a soft polyethylene counterpart. Cathodoluminescence emissions from oxygen vacancies (FIG. 18D) increased by ~250% with respect to pristine alumina heads; these were matched by a ~153% increase in O—Al—VO bonds detected by XPS (Al2p edge, FIG. 18E). Conversely, the number of Al—O—Al and O—Al—O—H bonds decreased by 34% and 26%, respectively.

Figure 19A:
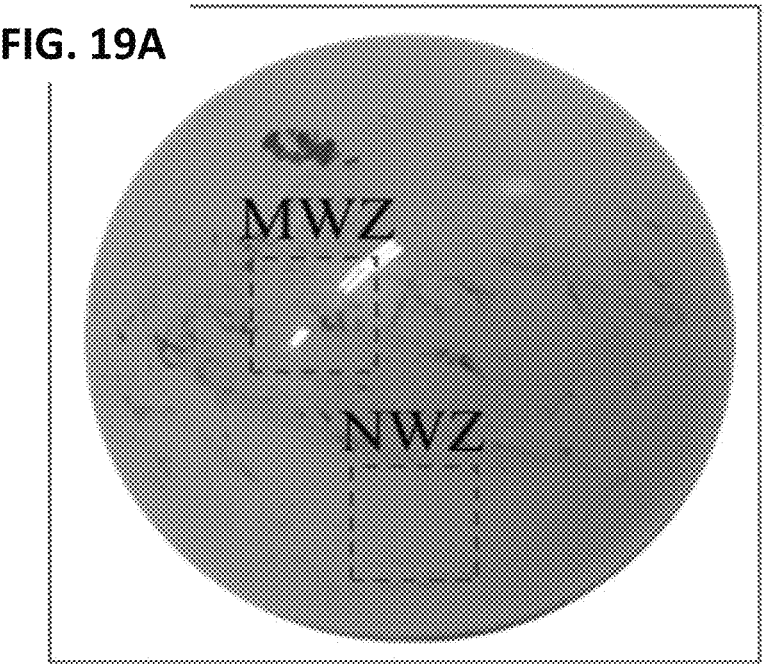
FIG. 19A shows a short-term in vivo exposed ZTA composite femoral head.
Figure 19B:
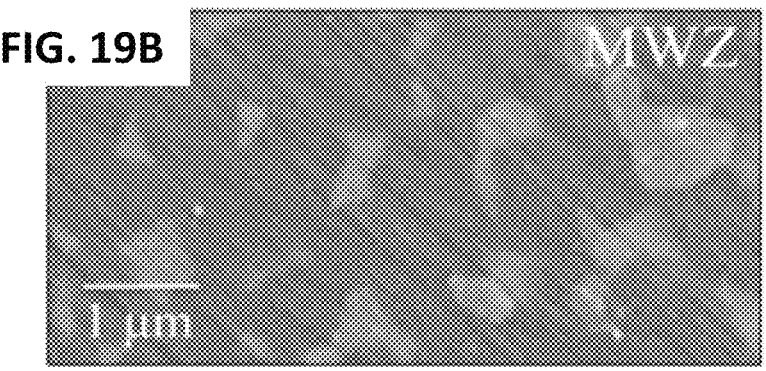
FIG. 19B shows the microstructure of a short-term in vivo exposed ZTA composite femoral head.
Figure 19C:
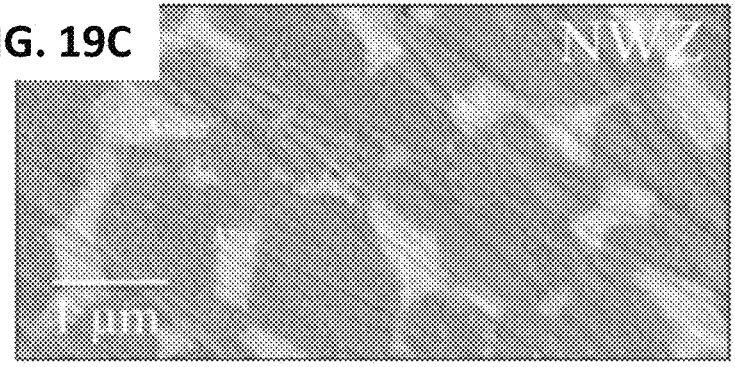
FIG. 19C shows its microstructure in the NWZ.
Figure 19D:
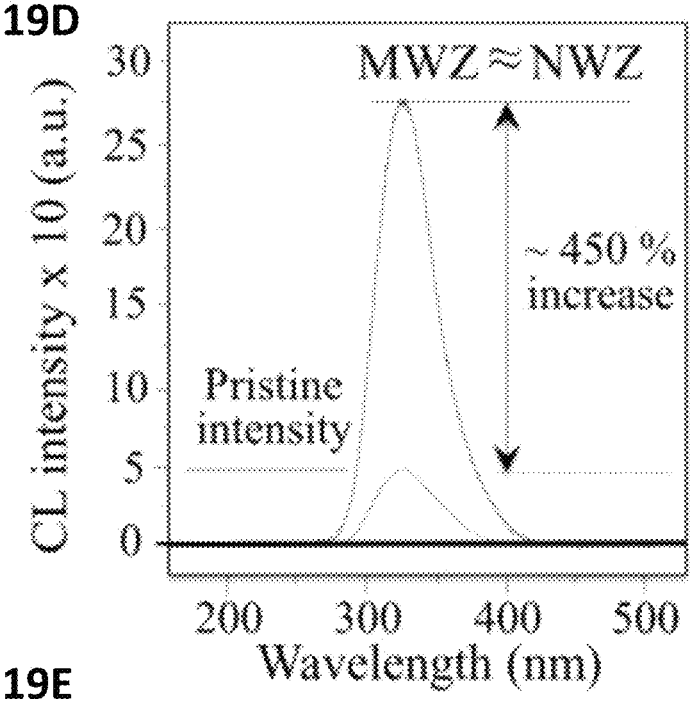
FIG. 19D shows its CL oxygen vacancy emission compared to that of a pristine ZTA sample.
Figure 19E:
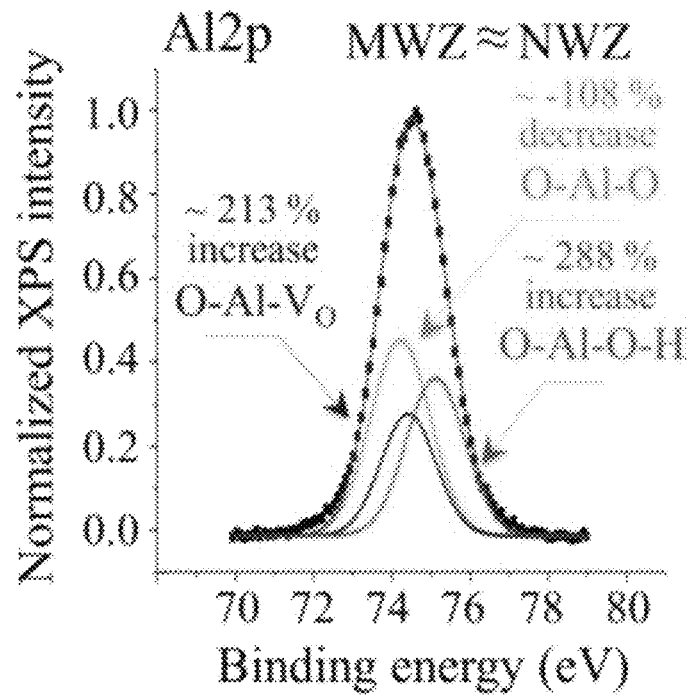
FIG. 19E shows its deconvoluted average XPS (Al2p) spectrum.

The photograph in FIG. 19A is that of a ZTA femoral head which articulated only for 20 months in vivo against an X3 liner, (i.e., the same liners tested in vitro, cf. FIGS. 12, 15, and 16). Metal contamination is visible on the head's surface due to several dislocation events, which preceded its revision surgery. The fine microstructure, imaged in the MWZ and NWZ by scanning electron microscopy (FIGS. 19B and 19C), respectively, consisted of $Al_2O_3$ (darker color) and $ZrO_2$ (whitish) grains with average sizes of ~1 and 0.4 μm, respectively. Both zones indicated that the head was essentially undamaged because typical machining marks from its manufacturing process were evident on its surface. The MWZ and NWZ emitted similar CL-intensities from oxygen vacancies, both of which were higher by ~450% compared to pristine components (FIG. 19D). XPS (Al2p) detected a ~213% increase in O—Al-Vo bonds (FIG. 19E) accompanied by a ~108% decrease in the atomic fraction of Al—O—Al bonds. However, unlike the monolithic alumina head described in FIGS. 18A-18E, the population of O—Al—O—H increased by ~288% with respect to pristine ZTA heads; this could be related to the presence of the $Cr^{3+}$ dopant in the alumina lattice which has a stronger hydrogen bond.

In substance, both CL and XPS independently detected a significantly higher population of oxygen vacancies at the surface of both long- and short-term femoral head retrievals made of alumina-based ceramics. Moreover, the off-stoichiometry observed on the retrievals' surfaces were significantly higher than those induced in the same materials during in vitro experiments. Characterization of these retrievals confirmed that a non-negligible amount of oxygen was released into the tribolayer from their surfaces. Indeed, the amount of oxygen released even from the short-term retrieval is striking. The combination of an acidic hydrothermal environment, which is typical of synovial fluid in osteoarthritic patients, along with stronger frictional forces than those applied in the in vitro experiments was likely responsible for the marked trend in its observed oxygen deficiency.

The disclosures shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the examples described above may be modified within the scope of the appended claims.

What is claimed is:

1. A method of preparing a silicon oxynitride material, wherein the silicon oxynitride material has improved wear performance, the method comprising:

forming a silicon nitride material block; and
oxidizing the silicon nitride material block,
wherein oxidizing the silicon nitride material block is performed using hydrothermal oxidation in a steam autoclave,
wherein the hydrothermal oxidation is conducted at a temperature ranging from about 100° C. to about 150° C.,
wherein the hydrothermal oxidation is conducted at a pressure of about 1 atmosphere to about 5 atmospheres, and
wherein the hydrothermal oxidation is conducted for a duration ranging from about 70 to about 150 hours.

2. The method of claim 1, wherein forming the silicon nitride material block comprises:
preparing a slurry comprising silicon, oxygen, and nitrogen, and further comprising at least one of yttrium oxide and aluminum oxide;
milling the slurry; and
drying the slurry to obtain a dried slurry.

3. The method of claim 1, wherein the silicon oxynitride material comprises a first crystalline phase and a first amorphous phase.

4. The method of claim 1, wherein the hydrothermal oxidation is conducted at a pressure of about 2 atmospheres.

5. The method of claim 1, wherein the hydrothermal oxidation is conducted at a temperature ranging from about 120° C. to about 135° C.

6. The method of claim 1, wherein the hydrothermal oxidation is conducted at a temperature of about 132° C.

7. The method of claim 1, wherein the hydrothermal oxidation is conducted for a duration of about 72 hours.

8. The method of claim 1, wherein the silicon nitride material block is an articulation component of a prosthetic joint.

9. The method of claim 8, wherein the articulation component is a femoral head.

10. The method of claim 8, wherein the improved wear performance increases the longevity of the prosthetic joint greater than 15 years.

11. The method of claim 8, wherein the silicon nitride material has a surface chemistry that protects a counter surface of the articulation component from oxidation.

12. The method of claim 11, wherein the counter surface is an acetabular polyethylene cup.

13. The method of claim 1, a surface of the silicon oxynitride material has periodic pits and defects that are filled with silica glass after the hydrothermal oxidation.

14. The method of claim 1, wherein a surface of the silicon oxynitride material has a reduction of O—Si—N bonds of about 10% to about 50% in favor of O—Si—O bonds and a reduction in N—Si—N bonds of about 10% to about 55% in favor of O—Si—O bonds as compared to a silicon oxynitride material that has not undergone hydrothermal oxidation.

15. The method of claim 1, wherein a surface of the silicon oxynitride material has a reduction of silicon amine functional groups of about 10% to about 55% in favor of silanol functional groups, resulting in a surface chemistry to lubricate the surface for wear as compared to a silicon oxynitride material that has not undergone hydrothermal oxidation.

* * * * *